US010155763B2

(12) United States Patent
Lee et al.

(10) Patent No.: US 10,155,763 B2
(45) Date of Patent: Dec. 18, 2018

(54) 2-PYRIDYL SUBSTITUTED IMIDAZOLES AS ALK5 AND/OR ALK4 INHIBITORS

(75) Inventors: Ju Young Lee, Suwon-si (KR); Keun-Ho Ryu, Seoul (KR); Jae-Sun Kim, Suwon-si (KR); Yong-Hyuk Kim, Suwon-si (KR); Dong-Chul Shin, Suwon-si (KR); Bong-yong Lee, Seoul (KR); Sang-hwan Kang, Suwon-si (KR); Hyun-Jung Lee, Seoul (KR); Hoechul Jung, Seoul (KR); Young Ah Shin, Yongin-si (KR); Euisun Park, Yongin-si (KR); Jaeseung Ahn, Seoul (KR); Hun-Taek Kim, Seoul (KR); Je Ho Ryu, Seongnam-si (KR)

(73) Assignee: TIUMBIO CO., LTD., Seongham-si (KR)

( * ) Notice: Subject to any disclaimer, the term of this patent is extended or adjusted under 35 U.S.C. 154(b) by 70 days.

(21) Appl. No.: 13/548,785

(22) Filed: Jul. 13, 2012

(65) Prior Publication Data

US 2013/0018052 A1 Jan. 17, 2013

Related U.S. Application Data

(60) Provisional application No. 61/507,305, filed on Jul. 13, 2011.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .................................................. C07D 487/04
See application file for complete search history.

(56) References Cited

U.S. PATENT DOCUMENTS

| 4,175,127 | A | * | 11/1979 | Bender et al. ................ 514/333 |
| 7,314,940 | B2 | * | 1/2008 | Graczyk .............. C07D 487/04 546/118 |
| 7,405,299 | B2 | * | 7/2008 | Beight et al. ................. 544/353 |
| 2004/0176390 | A1 | | 9/2004 | Blumberg et al. |

FOREIGN PATENT DOCUMENTS

| EP | 0231622 A2 | | 8/1987 | |
| EP | 403251 A2 | * | 12/1990 | ............. A61K 31/00 |
| JP | 62153286 A | | 7/1987 | |
| JP | 04273877 A | * | 9/1992 | ........... C07D 487/04 |
| JP | 04273877 A | * | 9/1992 | ........... C07D 487/04 |
| JP | 2006519249 A | | 8/2006 | |
| WO | 2007/018818 A1 | | 2/2007 | |

OTHER PUBLICATIONS

Harrison "Antagonists of activin signaling: mechanisms and potential biological applications" TRENDS in Endocrinology and Metabolism Mar. 2005 vol. 16 No. 2 73-78.*
Sharma "Idiopathic Pulmonary Fibrosis : Newer Concepts and Management Strategies" Indian J Chest Dis Allied Sci 2003; 45 : 31-49.*
Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*
Callahan "Identification of Novel Inhibitors of the Transforming Growth Factor B1 (TGF-B1) Type 1 Receptor (ALK5)" J. Med. Chem. 2002, 45, 999-1001.*
George A. Patani "Bioisosterism: A Rational Approach in Drug Design" Chemical Reviews 1996, 96, 3147-3176.*
Wermuth "Molecular Variations Based on Isosteric Replacements" Chapter 13 in The Practice of Medicinal Chemistry, Academic: 1996.*
Lima "Bioisosterism: A Useful Strategy for Molecular Modification" Current Medicinal Chemistry, 2005, vol. 12, No. 1 26-49.*
Heldin "Chapter 1 Transforming Growth Factor-β Signaling" in TGF-β in Human Disease, 2013 Springer: Japan.*
Ren "Pharmacophore modeling and virtual screening for the discovery of new transforming growth factor-b type I receptor (ALK5) inhibitors" European Journal of Medicinal Chemistry 44 (2009) 4259-4265.*
University of Cambridge John van Geest Centre for Brain Repair School of Clinical Medicine "Alzheimer's disease and tauopathy" Online "http://www.brc.cam.ac.uk/research/alzheimers-disease-and-tauopathy/" accessed Sep. 10, 2015.*
Tomohiro Chiba "Emerging Therapeutic Strategies in Alzheimer's Disease" Intech 2013, 181-225.*
Galie et. al. "Guidelines for the diagnosis and treatment of pulmonary hypertension" European Heart Journal (2009) 30, 2493-2537.*
Damia "Contemporary pre-clinical development of anticancer agents— What are the optimal preclinical models?" European Journal of Cancer 2009, 45, 2768-2781.*
Sharma "Cell line-based platforms to evaluate the therapeutic efficacy of candidate anticancer agents" Nature Reviews Cancer Apr. 2010, vol. 10, 241-253.*
Ocana, A. "Preclinical development of molecular targeted agents for cancer" Nat. Rev. Clin. Oncol. 2011, 8, 200-209.*
Ledford "US cancer institute overhauls cell lines" Nature Feb. 25, 2016 vol. 530 p. 391.*
Johnson, et. al. "Relationships between drug activity in NCI preclinical in vitro and in vivo models and early clinical trials." British Journal of Cancer 2001, 84, 1424-1431.*

(Continued)

*Primary Examiner* — David K O'Dell
(74) *Attorney, Agent, or Firm* — Sughrue Mion, PLLC

(57) ABSTRACT

The present invention provides a novel 2-pyridyl substituted imidazole derivative, or a pharmaceutically acceptable salt or solvate thereof, which selectively inhibits the transforming growth factor-β (TGF-β) type I receptor (ALK5) and/or the activin type I receptor (ALK4); a pharmaceutical composition comprising same as an active ingredient; and a use of the 2-pyridyl substituted imidazole derivative for the manufacture of a medicament for preventing or treating a disease mediated by ALK5 and/or ALK4 receptors in a mammal.

8 Claims, No Drawings

(56) References Cited

OTHER PUBLICATIONS

Lopez-de la Mora "Role and New Insights of Pirfenidone in Fibrotic Diseases" Int. J. Med. Sci. 2015, vol. 12, 841-847.*
"Chapter 5. Cardiovascular Drugs" in Drug Discovery : Practices, Processes, and Perspectives, edited by Jie Jack Li, and E. J. Corey, Wiley, 2013, 141-204.*
A.M. Bendele "Animal models of rheumatoid arthritis" J Musculoskel Neuron Interact 2001; 1(4):377-385.*
Bendele, "Animal Models of Arthritis: Relevance to Human Disease" Toxicol Pathol 1999 27: 134-142.*
European Patent Office, Communication dated Nov. 14, 2014 issued in corresponding application No. 12811865.0.
Singh et al, "Successful discovery of TBRI (ALK5) kinase inhibitors using HTS, target-hopping and virtual screening," Chemistry Today, May/Jun. 2005, vol. 23, No. 3, pp. 35-37.
Jin et al, "Synthesis and biological evaluation of 1-substituted-3(5)-(6-methylpyridin-2-yl)-4-(quinoxalin-6-yl)pyrazoles as transforming growth factor-β type 1 receptor kinase inhibitors," European Journal of Medicinal Chemistry, 2011, vol. 46, pp. 3917-3925.
Ren et al, "Pharmacophore modeling and virtual screening for the discovery of new transforming growth factor-β type I receptor (ALK5) inhibitors," European Journal of Medicinal Chemistry, 2009, vol. 44, pp. 4259-4265.
Kim et al, "Synthesis and biological evaluation of 4(5)-(6-methylpyridin-2-yl)imidazoles and -pyrazoles as transforming growth factor-β type 1 receptor kinase inhibitors," Bioorganic & Medicinal Chemistry, 2010, vol. 18, pp. 4459-4467.
C.G. Wermuth, The Practice of Medical Chemistry, pp. 235-271 (1988), 40 pgs. total.
Japan Patent Office, Communication dated Mar. 1, 2016, issued in corresponding Japanese Application No. 2014-520137.
Grygielko, et al., "Inhibition of Gene Markers of Fibrosis with a Novel Inhibitor of Transforming Growth Factor-β Type I Receptor Kinase in Puromycin-Induced Nephritis," JPET, 313(3):943-951 (2005).
Moon, et al., "IN-1130, a novel transforming growth factor-β type I receptor kinase (ALK5) inhibitor, suppresses renal fibrosis in obstructive nephropathy," Kidney International, 70:1234-1243 (2006). doi:10.1038/sj.ki.5001775; published online Aug. 23, 2006.
Petersen, et al., "Oral administration of GW788388, an inhibitor of TGF-β type I and II receptor kinases, decreases renal fibrosis," Kidney International, 73:705-715 (2008).
Sun, et al., "Inhibition of intimal hyperplasia in murine aortic allografts by the oral administration of the transforming growth factor-beta receptor I kinase inhibitor SD-208," J. Heart Lung Transplant., 33:654-661 (2014).
Park, et al., "EW-7197 inhibits hepatic, renal, and pulmonary fibrosis by blocking TGF-β/Smad and ROS signaling," Cell. Mo. Life Sci., published online: Dec. 9, 2014.
De Gouville, et al., "Inhibition of TGF-β signaling by an ALK5 inhibitor protects rats from dimethylnitrosamine-induced liver fibrosis," British Journal of Pharmacolology, 145:166-177 (2005).
Kim, et al., "TGF-β Type I Receptor Kinase Inhibitor EW-7197 Suppresses Cholestatic Liver Fibrosis by Inhibiting HIF1α-Induced Epithelial Mesenchymal Transition," Cell. Physiol. Biochem., 38:571-588 (2016).
Nakamura, et al., "Inhibition of Transforming Growth Factor β Prevents Progression of Liver Fibrosis and Enhances Hepatocyte Regeneration in Dimethylnitrosamine-Treated Rats," Hepatology, 32:247-255 (2000).
Higashiyama, et al., "Inhibition of activin receptor-like kinase 5 attenuates Bleomycin-induced pulmonary fibrosis," Experimental and Molecular Pathology, 83:39-46 (2007).
Bonnlaud, et al., "Progressive Transforming Growth Factor β1-induced Lung Fibrosis Is Blocked by an Orally Active ALK5 Kinase Inhibitor," Am. J. Respir. Crit. Care Med., 171:889-898 (2005).
Arribillaga, et al., "Therapeutic effect of a peptide inhibitor of TGF-β on pulmonary fibrosis," Cytokine, 53:327-333 (2011).

Terashima, et al., "R-268712, an orally active transforming growth factor-β type I receptor inhibitor, prevents glomerular sclerosis in a Thy1 nephritis model," European Journal of Pharmacology, 734:60-66 (2014).
Border, et al., "Suppression of experimental glomerulonephritis by antiserum against transforming growth factor β1," Nature, 346:371-374 (Jul. 1990).
Chang, et al., "Transforming growth factor-β1 and diabetic nephropathy," Am. J. Physiol. Renal Physiol., 310:F689-F696 (2016).
Chen, et al., "Diabetic Nephropathy and Transforming Growth Factor-β: Transforming Our View of Glomerulosclerosis and Fibrosis Build-Up," Seminars in Nephrology, 23(6):532-543 (Nov. 2003).
Reeves, et al., "Transforming growth factor β contributes to progressive diabetic nephropathy," PNAS, 97(14):7667-7669 (Jul. 5, 2000).
Saxena, et al., "Dual Roles of Immunoregulatory Cytokine TGF-β in the Pathogenesis of Autoimmunity-Mediated Organ Damage," J. Immunol., 180:1903-1912 (2008).
Lavoi, et al., "Neutralization of transforming growth factor-β attenuates hypertension and prevents renal injury in uremic rats," J. Hypertension, 23:1895-1903 (2005).
Sato, et al., "Targeted disruption of TGF-β1/Smad3 signaling protects against renal tubulointerstitial fibrosis induced by unilateral ureteral obstruction," Journal Clinical Investigation, 112(10):1486-1494 (Nov. 2003).
Moon, et al., "IN-1130, a novel transforming growth factor-β type I receptor kinase (ALK5) inhibitor, suppresses renal fibrosis in obstructive nephropathy," Kidney International, 70:1234-1243 (2006).
Khanna, et al., "Transforming Growth factor (TGF)-[beta] Mimics and Anti-TGF-[gbeta] Antibody Abrogates the in vivo effects of Cyclosporine: Demonstration of a Direct Role of TGF[beta] in Immunisuppression and Nephrotoxicity of Cyclosporine," Transplantation, 67(6):882-889 (Mar. 27, 1999).
Wolf, et al., "Cyclosporine Stimulates Expression of Transforming Growth Factor-β in Renal Cells," Transplantation, 60(3):237-241 (Aug. 1, 1995).
Zhou, et al., "Pirfenidone Inhibits Obliterative Airway Disease in Mouse Tracheal Allografts," J. Heart Lung Transplant., 24:1577-1585 (2005).
Wesselkamper, et al., "Gene Expression Changes during the Development of Acute Lung Injury: Role of Transforming Growth Factor β," Am. J. Respir. Crit. Care Med., 172:1399-1411 (2005).
Koh, et al., "Inhibition of transforming growth factor-β via the activin receptor-like kinase-5 inhibitor attenuates pulmonary fibrosis," Molecular Medicine Reports, 11:3808-3813 (2015).
Luo, et al., "Downregulation of Secretory Leukocyte Proteinase Inhibitor in Chronic Obstructive Lung Disease: The Role of TGF-β/Smads Signaling Pathways," Archives of Medical Research, 39:388-396 (2008).
Pittet, et al., "TGF-β is a critical mediator of acute lung injury," J. Clin. Invest., 107:1537-1544 (2001).
Wang, et al., "Reduction of bleomycin induced lung fibrosis by transforming growth factor β soluble receptor in hamsters," Thorax, 54:805-812 (1999).
Giri, et al., "Effect of antibody to transforming growth factor β on bleomycin induced accumulation of lung collagen in mice," Thorax, 48:959-966 (1993).
Tan, et al., "Targeted inhibition of activin receptor-like kinase 5 signaling attenuates cardiac dysfunction following myocardial infarction," Am. J. Physiol. Heart Circ. Physiol., 298:H1415-H1425 (2010).
Lee, et al., "Pirfenidone Prevents the Development of a Vulnerable Substrate for Atrial Fibrillation in a Canine Model of Heart Failure," Circulation, 114:1703-1712 (2006).
Waghabi, et al., "Pharmacological Inhibition of Transforming Growth Factor β Signaling Decreases Infection and Prevents Heart Damage in Acute Chagas' Disease," Antimicrobial Agents and Chemotherapy, 53(11):5694-4701 (2009).
Fu, et al., "SM16, an Orally Active TGF-β Type I Receptor Inhibitor Prevents Myofibroblast Induction and Vascular Fibrosis in the Rat Carotid Injury Model," Arterioscler. Thromb. Vasc. Biol., 28:665-671 (2008).

(56) References Cited

OTHER PUBLICATIONS

Sapitro, e al., "Suppression of transforming growth factor-β effects in rabbit subconjunctival fibroblasts by activin receptor-like kinase 5 inhibitor," Molecular Vision, 16:1880-1892 (2010).
Xiao, et al., "SB-431542 Inhibition of Scar Formation after Filtration Surgery and Its Potential Mechanism," Invest. Ophthalmol. Vis. Sci., 50:1698-1706 (2009) DOI:10.1167/iovs.08-1675.
Nassar, et al., "A TGF-β receptor 1 inhibitor for prevention of proliferative vitreoretinopathy," Experimental Eye Research, 123:72-86 (2014).
Zhang, et al., "Galangin inhibits hypertrophic scar formation via ALK5/Smad2/3 signaling pathway," Mol. Cell Biochem., 413:109-118 (2016). DOI 10.1007/s11010-015-2644-3.
Shah, et al., "Control of scarring in adult wounds by neutralising antibody to transforming growth factor β," Lancet, 339:213-214 (1992).
Ishida, et al., "Intracellular TGF-β Receptor Blockade Abrogates Smad-Dependent Fibroblast Activation In Vitro and In Vivo," Journal of Investigative Dermatology, 126:1733-1744. doi:10.1038/sj.jid.5700303; published online Jun. 1, 2006.
Ohsawa, et al., "An inhibitor of transforming growth factor beta type I receptor ameliorates muscle atrophy in a mouse model of caveolin 3-deficient muscular dystrophy," Laboratory Investigations, 92:1100-1114 (2012).
Ryu, et al., "Transforming Growth Factor-β Type I Receptor Inhibitor Induces Functional and Morphologic Recovery in a Rat Model of Erectile Dysfunction and Cavernous Fibrosis," Korean J. Androl., 30(1):23-30 (2012). http://dx.doi.org/10.5534/kja.2012.30.1.2 3.
Bueno, et al., "Semi-mechanistic modelling of the tumour growth inhibitory effects of LY2157299, a new type I receptor TGF-β kinase antagonist, in mice," European Journal of Cancer, 44:142-150 (2008).
Rodon, et al, "First-in-Human Dose Study of the Novel Transforming Growth Factor-β Receptor I Kinase Inhibitor LY2157299 Monohydrate in Patients with Advanced Cancer and Glioma," Clin. Cancer Res., 21(3):553-560 (2014).
Suzuki, et al., "A Novel Small-Molecule Inhibitor of Transforming Growth Factor β Type I Receptor Kinase (SM16) Inhibits Murine Mesothelioma Tumor Growth In vivo and Prevents Tumor Recurrence after Surgical Resection," Cancer Res., 67(5):2351-2359 (Mar. 1, 2007).
Gaspar, et al., "Inhibition of Transforming Growth Factor β Signaling Reduces Pancreatic Adenocarcinoma Growth and Invasiveness," Mol. Pharmacol., 72:152-161 (2007).
Shinto, et al., "Combination effect of a TGF-β receptor kinase inhibitor with 5-FU analog S1 on lymph node metastasis of scirrhous gastric cancer in mice," Cancer Sci., 101(8):1846-1852 (Aug. 2010).
Park, et al., "EW-7195, a novel inhibitor of ALK5 kinase inhibits EMT and breast cancer metastasis to lung," European Journal of Cancer, 47:2642-2653 (2011).
Son, et al., "EW-7197, a Novel ALK-5 Kinase Inhibitor, Potently Inhibits Breast to Lung Metastasis," Mol. Cancer Ther., 13(7):1704-1716 (Jul. 2014).
Park, et al., "An novel inhibitor of TGF-β type I receptor, IN-1130, blocks breast cancer lung metastasis through inhibition of epithelial-mesenchymal transition," Cancer Lett., (2014), http://dx.doi.org/10.1016/j.canlet.2014.05.006.

Wan, et al., "Effect of transforming growth factor beta (TGF-β) receptor I kinase inhibitor on prostate cancer bone growth," Bone, 50:695-703 (2012).
Uhl, et al., "SD-208, a Novel Transforming Growth Factor β Receptor I Kinase Inhibitor, Inhibits Growth and Invasiveness and Enhances Immunogenicity of Murine and Human Glioma Cells In vitro and In vivo," Cancer Research, 64:7954-7961 (Nov. 1, 2004).
Bandyopadhyay, et al., Inhibition of Pulmonary and Skeletal Metastasis by a Transforming Growth Factor-β Type I Receptor Kinase Inhibitor, Cancer Res., 66(13):6714-6721 (Jul. 1, 2006).
Ehata, et al., "Ki26894, a novel transforming growth factor-β type I receptor kinase inhibitor, inhibits in vitro invasion and in vivo bone metastasis of a human breast cancer cell line," Cancer Sci., 98(1):127-133 (Jan. 2007).
Arteaga, et al. "Anti-Transforming Growth Factor (TGF)-β Antibodies Inhibit Breast Cancer Cell Tumorigenicity and Increase Mouse Spleen Natural Killer Cell Activity: Implications for a Possible Role of Tumor Cell/Host TGF-β Interactions in Human Breast Cancer Progression," J. Clin. Invest., 92:2569-2576 (1993).
Melisi, et al., "LY2109761, a novel transforming growth factor β receptor type I and type II dual inhibitor, as a therapeutic approach to suppressing pancreatic cancer metastasis," Mol. Cancer Ther., 7(4):829-840 (Apr. 2008).
Park, et al., "SKI2162, an inhibitor of the TGF-β type I receptor (ALK5), inhibits radiation-induced fibrosis in mice," Oncotarget, 6(6):4171-4179 (2015).
Xavier, et al., Amelioration of Radiation-induced Fibrosis: Inhibition of Transforming Growth Factor-β Signaling by Halofuginone, J. Biol. Chem., 279(15):15167-15176 (2004).
Anscher, et al., "Small Molecular Inhibitor of Transforming Growth Factor-β Protects Against Development of Radiation-Induced Lung Injury," Int. J. Radiation Oncology Biol. Phys., 71(3):829-837 (2008).
Anscher, et al., "Antitransforming Growth Factor-β Antibody 1d11 Ameliorates Normal Tissue Damage Caused by High-Dose Radiation," Int. J. Radiation Oncology Biol. Phys., 65(3):876-881 (2006).
Oliveira, et al., "Oral Administration of GW788388, an Inhibitor of Transforming Growth Factor Beta Signaling, Prevents Heart Fibrosis in Chagas Disease," PLoS Negl. Trop. Dis., 6(6): e1696, doi:10.1371/journal.pntd.0001696, Jun. 12, 2012.
Sakuma, et al., "TGF-beta type I receptor kinase inhibitor down-regulates rheumatoid synoviocytes and prevents the arthritis induced by type II collagen antibody," International Immunology, 19(2):117-126 doi:10.1093/intimm/dxl128., Nov. 29, 2006.
Mohammad, et al., Pharmacologic Inhibition of the TGF-beta Type I Receptor Kinase Has Anabolic and Anti-Catabolic Effects on Bone, PLoS ONE, 4(4):e5275 doi:10.1371/journal.pone.0005275, Apr. 16, 2009.
Manaenko, et al, "Inhibition of Transforming Growth Factor-beta Attenuates Brain Injury and Neurological Deficits in a Rat Model of Germinal Matrix Hemorrhage," Stroke, 45:828-834, Jan. 14, 2014.
Bandyopadhyay, et al., "Doxorubicin in Combination with a Small TGF-beta Inhibitor: A Potential Novel Therapy for Metastatic Breast Cancer in Mouse Models," PloS ONE, 5(4): e10365. Doi:10.1371/journal.phone.0010365, Apr. 28, 2010.

\* cited by examiner

2-PYRIDYL SUBSTITUTED IMIDAZOLES AS ALK5 AND/OR ALK4 INHIBITORS

FIELD OF THE INVENTION

The present invention relates to a novel 2-pyridyl substituted imidazole derivative or a pharmaceutically acceptable salt thereof which selectively inhibits the transforming growth factor-β (TGF-β) type I receptor (ALK5) and/or the activin type I receptor (ALK4); a pharmaceutical composition comprising same as an active ingredient; and a use of the 2-pyridyl substituted imidazole derivative for the manufacture of a medicament for preventing or treating a disease mediated by ALK5 and/or ALK4 receptors in a mammal.

BACKGROUND OF THE INVENTION

TGF-β is a reacted protein that exists in at least three isoforms called TGF-β1, TGF-β2 and TGF-β3, and it controls cell proliferation and differentiation, wound healing, extracellular matrix production and immune-suppression. Other members of the transforming growth factor superfamily include activins, inhibins, bone morphogenetic proteins, growth and differentiation factors, and Müllerian inhibiting substance.

TGF-β1 transduces signals through two highly conserved single transmembrane serine/threonine kinases, the type I (ALK5) and type II TGF-β receptors. Upon ligand-induced oligomerization, the type II receptor hyperphosphorylates serine/threonine residues in the GS region of ALK5, which leads to the activation of ALK5 by creating a binding site for Smad proteins. The activated ALK5 in turn phosphorylates Smad2 and Smad3 proteins at the C-terminal SSXS-motif, thereby causing their dissociation from the receptor and heteromeric complex formation with Smad4. Smad complexes translocate to the nucleus, assemble with specific DNA-binding co-factors and co-modulators, to finally activate the transcription of extracellular matrix components and inhibitors of matrix-degrading proteases.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Numerous experimental animal studies have demonstrated that the glomerular expression of TGF-β is associated with fibrosis. Such studies include Thy-1 rat model of proliferative glomerulonephritis, anti-GBM glomerulonephritis in rabbits, and 5/6 nephrectomy rat model of focal segmental glomerulosclerosis, as has been recently reviewed (see, Bitzer, M. et al., *Kidney Blood Press. Res.* 21:1-12 (1998)). Neutralizing antibodies against TGF-β improve glomerular histology in Thy-1 nephritis model (see, Border, W. A. et al., *Nature* 346: 371-374 (1990)).

Hyperglycemic conditions promote the TGF-β mRNA and protein syntheses in both murine proximal tubule cells and human mesangial cells (see, Wahab, N. A. et al., *Biochem. J.* 316:985-992 (1996); Rocco, M. V. et al., *Kidney Int.* 41: 107-114 (1992)). Diabetic patients with an early kidney disease show increased accumulation of TGF-β mRNA and the expressed protein within the glomerulus (see, Yoshioka, K. et al., *Lab. Invest.* 68: 154-163 (1993)). Kidneys with chronic renal interstitial fibrosis exhibit thickened tubular basement membranes and an expanded interstitial compartment, with interstitial fibrosis characterized by an increase in collagens I, III, V, VII, and fibronectin (see, Eddy, A. A., *J. Am. Soc. Nephrol.* 7: 2495-2508 (1996)).

TGF-β gene expression and TGF-β protein production have been observed to increase in a variety of animal models of pulmonary fibrosis caused by bleomycin, silica, asbestos, and radiation (see, Phan, S. H. and Kunkel, S. L., *Exp. Lung Res.* 18: 29-43 (1992); Williams, A. O. et al., *Am. J. Pathol.* 142: 1831-1840 (1993); Rube, C. E. et al., *Int. J. Radiat. Oncol. Biol. Phys.* 47: 1033-1042 (2000)). Coincident increase in TGF-β1 protein and collagen gene expression in adjacent tissue slices from idiopathic pulmonary fibrosis is observed in human pulmonary fibrotic diseases (see, Broekelmann, T. J. et al., *Proc. Natl. Acad. Sci. USA* 88:6642-6646 (1991)). Increased TGF-β production has been observed for patients with sarcoidosis, pneumoconiosis, asbestosis, and radiation-induced fibrosis (see, Khalil, N. et al., *Am. J. Respir. Cell. Mol. Biol.* 14:131-138 (1996); Jagirdar, J. et al., *Environ. Health Perspect.* 105:1197-1203 (1997)). Anti-TGF-β antibodies and TGF-β-soluble receptors could partially inhibit fibrosis in bleomycin-induced lung fibrosis rodent models (see, Giri, S. N. et al., *Thorax* 48: 959-966 (1993); Wang, Q. et al., *Thorax* 54: 805-812 (1999)). Tobacco smoke has been implicated as one of the most important factors that cause small airway disorders, leading to chronic obstructive pulmonary disease (COPD) (see, Wright, J. M. et al., *Am. Rev. Respir. Dis.* 146: 240-262 (1992)). COPD is a slowly progressive and irreversible disorder characterized by the functional abnormality of airway obstruction. TGF-β has been hypothesized to be involved in airway remodeling of the chronic airway inflammatory disorders such as COPD (see, Takizawa, H. *Int. J. Mol. Med.* 1: 367-378 (1998); Ning, W. et al., *Proc. Natl. Acad. Sci. USA* 101:14895-14900 (2004)).

Hepatic stellate cells (HSC) are the major source of extracellular matrix proteins in hepatic fibrosis. Extracellular matrix production by activated hepatic stellate cells markedly increases by the action of TGF-β1 (see, Friedman, S. L., *Prog. Liver Dis.* 14: 101-130 (1996); Pietrangelo, A., *Semin. Liver Dis.* 16:13-30 (1996)). Transgenic mice that overexpress TGF-β1 in the liver develop hepatic fibrosis as well as extrahepatic pathologies such as renal fibrosis (see, Sanderson, N. et al., *Proc. Natl. Acad. Sci. USA* 92:2572-2576 (1995)).

TGF-β1 and its receptors are overexpressed in injured blood vessels and in fibroproliferative vascular lesions, leading to overproduction of extracellular matrix (see, Saltis, J. et al., *Clin. Exp. Pharmacol. Physiol.* 23: 193-200 (1996); McCaffrey, T. A. et al., *J. Clin. Invest.* 96: 2667-2675 (1995)).

Anti-TGF-β antibodies reduce scar formation with the improvement of the cytoarchitecture of the neodermis in rats (see, Shah, M., *J. Cell. Sci.* 108: 985-1002 (1995)), promote the healing of corneal wounds in rabbits (see, Moller-Pedersen, T., *Curr Eye Res.* 17:736-747 (1998)), and accelerate wound healing of gastric ulcers in rats (see, Ernst, H., *Gut* 39: 172-175 (1996)).

Radiation fibrosis is a frequent sequel of therapeutic or accidental radiation overexposure of normal human tissues. TGF-β1 plays a key role in the initiation, development, and persistence of radiation fibrosis, as has been recently reviewed (see, Martin, M. et al., *Int. J. Radiat. Oncol. Biol. Phys.* 47:277-290 (2000)).

Organ transplantation is often complicated by chronic rejection, which for some organs such as the kidney, becomes the major causes of graft loss. In human patients, chronic rejection of lung and kidney transplants is associated with increased expression of TGF-β within the tissue (see, El-Gamel, A. et al., *Eur. J. Cardiothorac. Sung.* 13: 424-430 (1998); Shihab, F. S. et al., *J. Am. Soc. Nephrol.* 6:286-294 (1995)).

TGF-β is implicated in peritoneal adhesions (see, Saed, G. M. et al., *Wound Repair Regeneration* 7: 504-510 (1999)). The peritoneal and sub-dermal fibrotic adhesions may be prevented by administering ALK5 and/or ALK4 inhibitors.

The tumor cells and the stromal cells within the tumors in late stages of various cancers generally overexpress TGF-β. This leads to stimulation of angiogenesis and cell motility, suppression of the immune system, and increased interaction of tumor cells with the extracellular matrix (see, Hojo, M. et al., *Nature* 397: 530-534 (1999)). Consequently, the tumor cells become more invasive and metastasize to other organs (see, Maehara, Y. et al., *J. Clin. Oncol.* 17: 607-614 (1999); Picon, A. et al., *Cancer Epidemiol. Biomarkers Prev.* 7:497-504 (1998)).

Plasminogen activator inhibitor-1 (PAI-1) is a major physiological inhibitor of both tissue-type plasminogen activator and urokinase-type plasminogen activator. Elevated levels of PAI-1 are associated with thrombosis and vascular disease, suggesting that high plasma PAI-1 may promote a hypercoagulable state by disrupting the natural balance between fibrinolysis and coagulation (see, Vaughan, D. E., *J. Invest. Med.* 46: 370-376 (1998)). It is known that TGF-β stimulates the expression of PAI-1 (see, Dennler, S. et al., *EMBO J.* 17: 3091-3100 (1998)). Accordingly, the inhibition of the production of PAI-1 with an inhibitor of the TGF-β signaling pathway would lead to novel fibrinolytic therapy.

Activin signaling and overexpression of activin are linked to pathological disorders that involve extracellular matrix accumulation and fibrosis (see, Matsuse, T. et al., *Am. J. Respir Cell Mol. Biol.* 13:17-24 (1995); Inoue, S. et al., *Biochem. Biophys. Res. Comm.* 205:441-448 (1994); Matsuse, T. et al., *Am. J. Pathol.* 148:707-713 (1996); De Bleser et al., *Hepatology* 26:905-912 (1997); Pawlowski, J. E., et al., *J. Clin. Invest.* 100:639-648 (1997); Sugiyama, M. et al., *Gastroenterology* 114:550-558 (1998); Munz, B. et al., *EMBO J.* 18:5205-5215 (1999)), inflammatory responses (see, Rosendahl, A. et al., *Am. J. Respir Cell Mol. Biol.* 25:60-68 (2001)), cachexia or wasting (see, Matzuk, M. M. et al., *Proc. Natl. Acad. Sci. USA* 91:8817-8821 (1994); Coerver, K. A. et al., *Mol. Endocrinol.* 10:534-543 (1996); Cipriano, S. C. et al., *Endocrinology* 141:2319-2327 (2000)), diseases or pathological responses in the central nervous system (see, Logan, A. et al., *Eur J. Neurosci.* 11:2367-2374 (1999); Logan, A. et al., *Exp. Neurol.* 159: 504-510 (1999); Masliah, E. et al., *Neurochem. Int.* 39:393-400 (2001); De Groot, C. J. A. et al., *J. Neuropathol. Exp. Neurol.* 58:174-187 (1999); John, G. R. et al., *Nat. Med.* 8:1115-1121 (2002)) and hypertension (see, Dahly, A. J. et al., *Am. J. Physiol. Regul. Integr. Comp. Physiol.* 283: R757-767 (2002)). Studies have shown that TGF-β and activin can act together synergistically to induce extracellular matrix production (see, Sugiyama, M. et al., *Gastroenterology* 114:550-558 (1998)).

Therefore, it becomes evident that the inhibition of ALK5 and/or ALK4 phosphorylation of Smad2 and Smad3 by the compound of the present invention would be able to treat and prevent the above mentioned disorders related to said signaling pathways.

International Publication No. WO 00/61576, and U.S. Patent Application Publication No. US 2003/0149277 A1 disclose triarylimidazole derivatives and their use as ALK5 inhibitors. International Publication No. WO 01/62756 discloses pyridinylimidazole derivatives and their use as ALK5 inhibitors. International Publication No. WO 02/055077 discloses the use of imidazolyl cyclic acetal derivatives as ALK5 inhibitors. Also, International Publication No. WO 03/087304 discloses tri-substituted heteroaryls and their use as ALK5 and/or ALK4 inhibitors.

The present inventors have unexpectedly discovered that a class of 2-pyridyl substituted imidazoles function as potent and selective inhibitors of ALK5 and/or ALK4 receptors and therefore, have utility in the treatment and prevention of various diseases mediated by ALK5 and/or ALK4 receptors.

SUMMARY OF THE INVENTION

Therefore, it is an object of the present invention to provide a compound or a pharmaceutically acceptable salt thereof which selectively and effectively inhibits ALK5 and/or ALK4 receptors.

It is another object of the present invention to provide a pharmaceutical composition for preventing or treating a disease mediated by ALK5 and/or ALK4 receptors, which comprises said 2-pyridyl substituted imidazole derivative as an active ingredient.

It is a further object of the present invention to provide a use of said 2-pyridyl substituted imidazole derivative for the manufacture of a medicament for preventing or treating a disease mediated by ALK5 and/or ALK4 receptors in a mammal.

It is a further object of the present invention to provide a method for preventing or treating a disease mediated by ALK5 or ALK4 receptors, or both ALK5 and ALK4 receptors in a mammal, which comprises administering said 2-pyridyl substituted imidazole derivative to the mammal in need thereof In accordance with one aspect of the present invention, there is provided a compound of formula (I) or a pharmaceutically acceptable salt or solvate thereof:

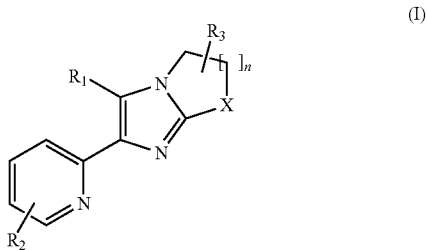

(I)

wherein, $R_1$ is phenyl, pyridyl or thienyl fused with a structural moiety which, together with two ring members of said phenyl, pyridyl or thienyl, forms a 5-7 membered aromatic or non-aromatic ring, wherein said ring optionally contains up to three heteroatoms independently selected from O, N and S, and the fused phenyl, pyridyl or thienyl ring is optionally substituted with one or more groups independently selected from halo, —O—$C_{1-6}$ alkyl, —S—$C_{1-6}$ alkyl, —$C_{1-6}$ alkyl, —$C_{1-6}$ haloalkyl, CN, —$(CH_2)_p$—$OR_4$, —O—$(CH_2)_q$—$NR_4R_5$, —$(CH_2)_p$—$NR_4R_5$, —NHCO—O—$(CH_2)_q$—$NR_4R_5$, —NHCO—$(CH_2)_p$—$NR_4R_5$, or —$C_{5-15}$ heteroaryl containg up to three heteroatoms independently selected from O, N and S; or $R_1$ is phenyl or pyridyl optionally substituted with one or more groups independently selected from halo, —O—$C_{1-6}$ alkyl, —S—$C_{1-6}$ alkyl, —$C_{1-6}$ alkyl, —$C_{1-6}$ haloalkyl, —CN, —$(CH_2)_p$—$OR_4$, —O—$(CH_2)_q$—$NR_4R_5$, —NH—$(CH_2)_q$—$NR_4R_5$, —$(CH_2)_p$—$NR_4R_5$, —$(CH_2)_p$—NHCOR$_4$, —$(CH_2)_p$NHCO$_2$R$_4$, —$(CH_2)_p$—NHSO$_2$R$_4$ or —$C_{5-15}$ heterocycle, said —$C_{5-15}$ heterocycle containing up to three heteroatoms independently selected from O, N and S and being optionally substituted with $C_{1-6}$ alkyl;

$R_2$ is H, halo, —O—$C_{1-6}$ alkyl, —S—$C_{1-6}$ alkyl, —$C_{1-6}$ alkyl, —$C_{3-7}$ cycloalkyl, —$C_{5-15}$ heteroaryl, —$C_{1-6}$ haloalkyl, —$(CH_2)_p$—$OR_4$, —O—$(CH_2)_p$—$NR_4R_5$, —$(CH_2)_p$—$NR_4R_5$, CN, —CONHR$_4$, or —SO$_2$NHR$_4$;

$R_3$ is H, —O—$C_{1-6}$ alkyl, —S—$C_{1-6}$ alkyl, —$C_{1-6}$ alkyl, —$C_{3-7}$ cycloalkyl, —$(CH_2)_p$NR$_4$R$_5$, —O—$(CH_2)_q$—NR$_4$R$_5$, —$(CH_2)_p$—CONHOH, —$(CH_2)_p$—CN, —$(CH_2)_p$—CO$_2$R$_4$, —$(CH_2)_p$—CONR$_4$R$_5$, —$(CH_2)_p$-tetrazole, —$(CH_2)_p$—COR$_4$, —$(CH_2)_q$—$(OR_6)_2$, —$(CH_2)_p$OR$_4$, —$(CH_2)_p$—CH═CH—CN, —$(CH_2)_p$—CH═CH—CO$_2$R$_4$, —$(CH_2)_p$—CH═CH—CONR$_4$R$_5$, —$(CH_2)_p$—NHCOR$_4$, —$(CH_2)_p$—NHCO$_2$R$_4$, —$(CH_2)_p$—NHSO$_2$R$_4$, or —$(CH_2)_p$—CH═CH-tetrazole;

$R_4$ and $R_5$ are independently H or —$C_{1-6}$ alkyl; or $R_4$ and $R_5$, together with the nitrogen atom to which they are attached, form a 3 to 6-membered aromatic or non-aromatic ring, wherein said ring optionally contains up to three heteroatoms independently selected from O, N, and S;

$R_6$ is —$C_{1-6}$ alkyl;

p is an integer ranging from 0 to 4;

q is an integer ranging from 2 to 5;

n is an integer ranging from 1 to 3;

X is NR$_7$, O, or S; and $R_7$ is H, OH, —$C_{1-6}$ alkyl, —$C_{3-7}$ cycloalkyl, or —CO—$C_{1-6}$ alkyl.

In accordance with another aspect of the present invention, there is provided a pharmaceutical composition for preventing or treating a disease mediated by ALK5 and/or ALK4 receptors, which comprises the compound of formula (I) or a pharmaceutically acceptable salt or solvate thereof as an active ingredient, and a pharmaceutically acceptable diluent or carrier.

In accordance with a further aspect of the present invention, there is provided a use of compound of formula (I) or a pharmaceutically acceptable salt or solvate thereof for the manufacture of a medicament for preventing or treating a disease mediated by ALK5 and/or ALK4 receptors in a mammal.

In accordance with a still further aspect of the present invention, there is provided a method for preventing or treating a disease mediated by ALK5 or ALK4 receptors, or both ALK5 and ALK4 receptors in a mammal, which comprises administering the compound of formula (I) or a pharmaceutically acceptable salt or solvate thereof to the mammal in need thereof.

DETAILED DESCRIPTION OF THE INVENTION

In an embodiment of the present invention, there is provided a compound of formula (I), or a pharmaceutically acceptable salt or solvate thereof:

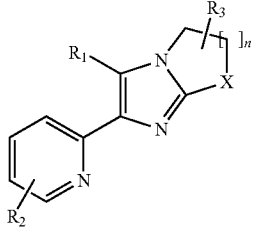

wherein, $R_1$ is phenyl, pyridyl or thienyl fused with a structural moiety which, together with two ring members of said phenyl, pyridyl or thienyl, forms a 5-7 membered aromatic or non-aromatic ring, wherein said ring optionally contains up to three heteroatoms independently selected from O, N and S, and the fused phenyl, pyridyl or thienyl ring is optionally substituted with one or more groups independently selected from halo, —O—$C_{1-6}$ alkyl, —S—$C_{1-6}$ alkyl, —$C_{1-6}$ alkyl, —$C_{1-6}$ haloalkyl, CN, —$(CH_2)_p$—OR$_4$, —O—$(CH_2)_q$—NR$_4$R$_5$, —$(CH_2)_p$—NR$_4$R$_5$, —NHCO—O—$(CH_2)_q$—NR$_4$R$_5$, —NHCO—$(CH_2)_p$—NR$_4$R$_5$, or —$C_{5-15}$ heteroaryl containing up to three heteroatoms independently selected from O, N and S; or $R_1$ is phenyl or pyridyl optionally substituted with one or more groups independently selected from halo, —O—$C_{1-6}$ alkyl, —S—$C_{1-6}$ alkyl, —$C_{1-6}$ alkyl, —$C_{1-6}$ haloalkyl, —CN, —$(CH_2)_p$—OR$_4$, —O—$(CH_2)_q$—NR$_4$R$_5$, —NH—$(CH_2)_q$—NR$_4$R$_5$, —$(CH_2)_p$—NR$_4$R$_5$, —$(CH_2)_p$—NHCOR$_4$, —$(CH_2)_p$—NHCO$_2$R$_4$, —$(CH_2)_p$—NHSO$_2$R$_4$ or $C_{5-15}$ heterocycle, said —$C_{5-15}$ heterocycle containing up to three heteroatoms independently selected from O, N and S and being optionally substituted with $C_{1-6}$ alkyl;

$R_2$ is H, halo, —O—$C_{1-6}$ alkyl, —S—$C_{1-6}$ alkyl, —$C_{1-6}$ alkyl, —$C_{3-7}$ cycloalkyl, —$C_{5-15}$ heteroaryl, —$C_{1-6}$ haloalkyl, —$(CH_2)_p$—OR$_4$, —O—$(CH_2)_p$—NR$_4$R$_5$, —$(CH_2)_p$—NR$_4$R$_5$, CN, —CONHR$_4$, or —SO$_2$NHR$_4$;

$R_3$ is H, —O—$C_{1-6}$ alkyl, —S—$C_{1-6}$ alkyl, —$C_{1-6}$ alkyl, —$C_{3-7}$ cycloalkyl, —$(CH_2)_p$—NR$_4$R$_5$, —O—$(CH_2)_q$—NR$_4$R$_5$, —$(CH_2)_p$—CONHOH, —$(CH_2)_p$—CN, —$(CH_2)_p$—CO$_2$R$_4$, —$(CH_2)_p$—CONR$_4$R$_5$, —$(CH_2)_p$-tetrazole, —$(CH_2)_p$—COR$_4$, —$(CH_2)_q$—$(OR_6)_2$, —$(CH_2)_p$—OR$_4$, —$(CH_2)_p$—CH═CH—CN, —$(CH_2)_p$—CH═CH—CO$_2$R$_4$, —$(CH_2)_p$—CH═CH—CONR$_4$R$_5$, —$(CH_2)_p$—NHCOR$_4$, —$(CH_2)_p$—NHCO$_2$R$_4$, —$(CH_2)_p$—NHSO$_2$R$_4$, or —$(CH_2)_p$—CH═CH-tetrazole;

$R_4$ and $R_5$ are independently H or —$C_{1-6}$ alkyl; or $R_4$ and $R_5$, together with the nitrogen atom to which they are attached, form a 3 to 6-membered aromatic or non-aromatic ring, wherein said ring optionally contains up to three heteroatoms independently selected from O, N, and S;

$R_6$ is –$C_{1-6}$ alkyl;

p is an integer ranging from 0 to 4;

q is an integer ranging from 2 to 5;

n is an integer ranging from 1 to 3;

X is NR$_7$, O, or S; and $R_7$ is H, OH, —$C_{1-6}$ alkyl, —$C_{3-7}$ cycloalkyl, or —CO—$C_{1-6}$ alkyl.

In another embodiment of the present invention, $R_1$ is phenyl, pyridyl or thienyl fused with a structural moiety which, together with two ring members of said phenyl, pyridyl or thienyl, forms a 5-6 membered aromatic or non-aromatic ring, wherein said ring optionally contains one or two heteroatoms independently selected from O, N and S, and the fused phenyl, pyridyl or thienyl ring is optionally substituted with one or more groups independently selected from halo, —O—$C_{1-6}$ alkyl, —S—$C_{1-6}$ alkyl, —$C_{1-6}$ alkyl, —$C_{1-6}$ haloalkyl, —CN, —$(CH_2)_p$—$OR_4$, —O—$(CH_2)_q$—$NR_4R_5$, —$(CH_2)_p$—$NR_4R_5$, —NHCO—$(CH_2)_q$—$NR_4R_5$, —NHCO—$(CH_2)_p$—$NR_4R_5$, or —$C_{5-15}$ heteroaryl containg up to three heteroatoms independently selected from O, N and S; or $R_1$ is phenyl optionally substituted with one or more groups independently selected from halo, —O—$C_{1-6}$ alkyl, —S—$C_{1-6}$ alkyl, —$C_{1-6}$ alkyl, —$C_{1-6}$ haloalkyl, CN, —NH—$(CH_2)_q$—$NR_4R_5$, —$(CH_2)_p$—$NR_4R_5$, —$(CH_2)_p$—$NHCOR_4$, —$(CH_2)_p$—$NHCO_2R_4$, —$(CH_2)_p$—$NHSO_2R_4$, or —$C_{5-15}$ heterocycle, said $C_{5-15}$ heterocycle containg up to three heteroatoms independently selected from O, N and S and being optionally substituted with $C_{1-6}$ alkyl.

In a further embodiment of the present invention, $R_1$ is a fused ring selected from the group consisting of quinoxalinyl, quinolinyl, thienopyridinyl, benzothiazolyl, benzothiophenyl, triazolopyridinyl, benzoxazolyl, quinolinyl, benzodioxolyl and benzodioxinyl, wherein said fused ring is optionally substituted with one or more groups independently selected from halo, —O—$C_{1-6}$ alkyl, —S—$C_{1-6}$ alkyl, —$C_{1-6}$ alkyl, —$C_{1-6}$ haloalkyl, —CN, —$(CH_2)_p$—$OR_4$, —O—$(CH_2)_q$—$NR_4R_5$, —$(CH_2)_p$—$NR_4R_5$, or —$C_{5-15}$ heteroaryl, said heteroaryl containing one or two heteroatoms independently selected from O, N and S; or $R_1$ is phenyl optionally substituted with one or two groups independently selected from halo, —O—$C_{1-6}$ alkyl, —S—$C_{1-6}$ alkyl, —$C_{1-6}$ alkyl, —$C_{1-6}$ haloalkyl, —CN, —$(CH_2)_p$—$OR_4$, —O—$(CH_2)_q$—$NR_4R_5$, —NH—$(CH_2)_q$—$NR_4R_5$, —$(CH_2)_p$—$NR_4R_5$, —$(CH_2)_p$—$NHCOR_4$, —$(CH_2)_p$—$NHCO_2R_4$, —$(CH_2)_p$—$NHSO_2R_4$ or —$C_{5-15}$ heterocycle, said heterocycle containing one or two heteroatoms independently selected from O, N and S and being optionally substituted with $C_{1-6}$ alkyl.

In a still further embodiment of the present invention, $R_1$ is benzo[1,3]dioxolyl, benzo[b]thiophenyl, 2,3-dihydrobenzo[1,4]dioxyl, benzooxazolyl, benzothiazolyl, quinoxalinyl, quinolinyl, [1,2,4]triazolo[1,5-α]pyridyl, thieno[3,2-c]pyridinyl, 2-pyrazol-1-yl-quinoxalinyl, dimethylaminoethyl-2-yloxy-quinoxalinyl, 2-methoxy-quinoxalinyl, 3,5-dimethoxyphenyl, 4-dimethylamino-phenyl, 4-benzonitrile, 2-methyl-quinolinyl, 4-aniline, 4-acetamino-phenyl, methylsulfonylaminophenyl, tert-butyl phenylcarbamate, 4-(4-methylpiperazin-1-yl)phenyl, morpholinophenyl, m-tolyl, 4-methoxyphenyl, 4-(trifluoromethyl)phenyl, 4-(methylthio)phenyl, 3-fluoro-4-methoxyphenyl or 4-fluorophenyl.

In one embodiment of the present invention, $R_2$ is halo, —O—$C_{1-6}$ alkyl, —S—$C_{1-6}$ alkyl, —$C_{1-6}$ alkyl, —$C_{3-7}$ cycloalkyl, —$C_{5-15}$ heteroaryl, —$C_{1-6}$ haloalkyl, —$(CH_2)_p$—$OR_4$, —O—$(CH_2)_p$—$NR_4R_5$, —$(CH_2)_p$—$NR_4R_5$, —CN, —$CONHR_4$, or —$SO_2NHR_4$.

In another embodiment of the present invention, $R_2$ is halo, —$C_{1-6}$ alkyl, —$C_{1-6}$ haloalkyl, or —$NH_2$, and is positioned ortho to the nitrogen of the pyridyl ring; preferably, $R_2$ is —$C_{1-4}$ alkyl.

In one embodiment of the present invention, $R_3$ is H, —O—$C_{1-6}$ alkyl, —S—$C_{1-6}$ alkyl, —$C_{1-6}$ alkyl, —$C_{3-7}$ cycloalkyl, —$(CH_2)_p$—$NR_4R_5$, —O—$(CH_2)_q$—$NR_4R_5$, —$(CH_2)_p$—CONHOH, —$(CH_2)_p$—CN, —$(CH_2)_p$—$CO_2R_4$, —$(CH_2)_p$—$CONR_4R_5$, —$(CH_2)_p$-tetrazole, —$(CH_2)_p$—$OR_4$, —$(CH_2)_p$—$NHCOR_4$, —$(CH_2)_p$—$NHCO_2R_4$, or —$(CH_2)_p$—$NHSO_2R_4$.

In another embodiment of the present invention, $R_3$ is H, —O—$C_{1-6}$ alkyl, —S—$C_{1-6}$ alkyl, —$C_{1-6}$ alkyl, —$(CH_2)_p$—$NR_4R_5$, —$(CH_2)_p$—CN, —$(CH_2)_p$—$CO_2R_4$, —$(CH_2)_p$—$CONR_4R_5$, —$(CH_2)_p$—$COR_4$, —$(CH_2)_p$—$OR_4$, or —$(CH_2)_p$—$NHCOR_4$.

In one embodiment of the present invention, $R_4$ and $R_5$ are independently H or —$C_{1-4}$ alkyl; or $R_4$ and $R_5$, together with the nitrogen atom to which they are attached, form a 3 to 6-membered aromatic or non-aromatic heterocyclic ring containing up to three heteroatoms independently selected from O, N and S, preferably, $R_4$ and $R_5$ are independently H or —$C_{1-6}$ alkyl In one embodiment of the present invention, p is an integer ranging from 0 to 2.

In one embodiment of the present invention, q is an integer ranging from 2 to 4.

In one embodiment of the present invention, n is an integer of 1 to 3; preferably, n is an integer of 1 or 2.

In one embodiment of the present invention, X is $NR_7$, O or S; preferably, X is $NR_7$.

In one embodiment of the present invention, $R_7$ is H, OH, —$C_{1-6}$ alkyl, or —CO—$C_{1-6}$ alkyl; preferably, H or —CO—$C_{1-6}$alkyl.

Specific compounds of the invention which may be mentioned include the following and pharmaceutically acceptable salts thereof:
1) 1-[6-(6-Methyl-pyridin-2-yl)-5-quinoxalin-6-yl-2,3-dihydro-imidazo[1,2-a]imidazol-1-yl]-ethanone;
2) 6-[2-(6-Methyl-pyridin-2-yl)-6,7-dihydro-5H-imidazo[1,2-a]imidazol-3-yl]-quinoxaline;
3) 6-[2-(6-Methyl-pyridin-2-yl)-5,6,7,8-tetrahydro-imidazo[1,2-a]pyrimidin-3-yl]-quinoxaline;
4) 6-[2-(6-Methyl-pyridin-2-yl)-6,7-dihydro-5H-imidazo[1,2-a]imidazol-3-yl]-quinoline;
5) 6-[2-(6-Methyl-pyridin-2-yl)-5,6,7,8-tetrahydro-imidazo[1,2-a]pyrimidin-3-yl]-quinoline;
6) 2-[2-(6-Methyl-pyridin-2-yl)-6,7-dihydro-5H-imidazo[1,2-a]imidazol-3-yl]-thieno[3,2-c]pyridine;
7) 6-[2-(6-Methyl-pyridin-2-yl)-6,7-dihydro-5H-imidazo[1,2-a]imidazol-3-yl]-benzothiazole; 8) 5-Benzo[b]thiophen-5-yl-6-(6-methyl-pyridin-2-yl)-2,3-dihydro-1H-imidazo[1,2-a]imidazole;
9) 6-[2-(6-Methyl-pyridin-2-yl)-6,7-dihydro-5H-imidazo[1,2-a]imidazol-3-yl]-[1,2,4]triazolo[1,5-a]pyridine;
10) 5-[2-(6-Methyl-pyridin-2-yl)-6,7-dihydro-5H-imidazo[1,2-a]imidazol-3-yl]-benzoxazole;
11) 4-[2-(6-Methyl-pyridin-2-yl)-6,7-dihydro-5H-imidazo[1,2-a]imidazol-3-yl]-quinoline;
12) 5-Benzo[1,3]dioxol-5-yl-6-(6-methyl-pyridin-2-yl)-2,3-dihydro-1H-imidazo[1,2-a]imidazole;
13) 5-(2,3-Dihydro-benzo[1,4]dioxin-6-yl)-6-(6-methyl-pyridin-2-yl)-2,3-dihydro-1H-imidazo[1,2-a]imidazole;
14) 7-[2-(6-Methyl-pyridin-2-yl)-6,7-dihydro-5H-imidazo[1,2-a]imidazol-3-yl]-2-pyrazol-1-yl-quinoxaline;
15) Dimethyl-(2-{7-[2-(6-methyl-pyridin-2-yl)-6,7-dihydro-5H-imidazo[1,2-a]imidazol-3-yl]-quinoxalin-2-yloxy}-ethyl)-amine;
16) 2-Methoxy-7-[2-(6-methyl-pyridin-2-yl)-6,7-dihydro-5H-imidazo[1,2-a]imidazol-3-yl]-quinoxaline;
17) 5-(3,5-Dimethoxyphenyl)-6-(6-methylpyridin-2-yl)-2,3-dihydro-1H-imidazo[1,2-a]imidazole;
18) N,N-Dimethyl-4-(6-(6-methylpyridin-2-yl)-2,3-dihydro-1H-imidazo[1,2-a]imidazol-5-yl)aniline;
19) 4-(6-(6-Methylpyridin-2-yl)-2,3-dihydro-1H-imidazo[1,2-a]imidazol-5-yl)benzonitrile;
20) 2-Methyl-6-(6-(6-methylpyridin-2-yl)-2,3-dihydro-1H-imidazo[1,2-a]imidazol-5-yl)quinoline;
21) 4-(6-(6-Methylpyridin-2-yl)-2,3-dihydro-1H-imidazo[1,2-a]imidazol-5-yl)aniline;

22) N-(4-(6-(6-Methylpyridin-2-yl)-2,3-dihydro-1H-imidazo[1,2-a]imidazol-5-yl)phenyl)acetamide;
23) N-(4-(6-(6-Methylpyridin-2-yl)-2,3-dihydro-1H-imidazo[1,2-a]imidazol-5-yl)phenyl)methanesulfonamide;
24) tert-Butyl (4-(6-(6-methylpyridin-2-yl)-2,3-dihydro-1H-imidazo[1,2-a]imidazol-5-yl)phenyl)carbamate;
25) 5-(4-(4-Methylpiperazin-1-yl)phenyl)-6-(6-methylpyridin-2-yl)-2,3-dihydro-1H-imidazo[1,2-a]imidazole;
26)₄-(4-(6-(6-Methylpyridin-2-yl)-2,3-dihydro-1H-imidazo[1,2-a]imidazol-5-yl)phenyl)morpholine;
27) 6-(6-Methylpyridin-2-yl)-5-(m-tolyl)-2,3-dihydro-1H-imidazo[1,2-a]imidazole;
28) 5-(4-Methoxyphenyl)-6-(6-methylpyridin-2-yl)-2,3-dihydro-1H-imidazo[1,2-a]imidazole;
29) 6-(6-Methylpyridin-2-yl)-5-(4-(trifluoromethyl) phenyl)-2,3-dihydro-1H-imidazo[1,2-a]imidazole;
30) 6-(6-Methylpyridin-2-yl)-5-(4-(methylthio) phenyl)-2,3-dihydro-1H-imidazo[1,2-a]imidazole;
31) 5-(3-Fluoro-4-methoxyphenyl)-6-(6-methylpyridin-2-yl)-2,3-dihydro-1H-imidazo[1,2-a]imidazole;
32) 5-(4-Fluorophenyl)-6-(6-methylpyridin-2-yl)-2,3-dihydro-1H-imidazo[1,2-a]imidazole;
33) 1-Acetyl-6-(6-methyl-pyridin-2-yl)-5-thieno[3,2-c]pyridin-2-yl-2,3-dihydro-1H-imidazo[1,2-a]imidazole-2-carboxylic acid ethyl ester;
34) 6-(6-Methyl-pyridin-2-yl)-5-thieno[3,2-c]pyridin-2-yl-2,3-dihydro-1H-imidazo[1,2-a]imidazole-2-carboxylic acid ethyl ester;
35) [6-(6-Methyl-pyridin-2-yl)-5-thieno[3,2-c]pyridin-2-yl-2,3-dihydro-1H-imidazo[1,2-a]imidazol-2-yl]-methanol;
36) 1-Acetyl-6-(6-methyl-pyridin-2-yl)-5-thieno[3,2-c]pyridin-2-yl-2,3-dihydro-1H-imidazo[1,2-a]imidazole-2-carbonitrile;
37)₆-(6-Methyl-pyridin-2-yl)-5-thieno[3,2-c]pyridin-2-yl-2,3-dihydro-1H-imidazo[1,2-a]imidazole-2-carbonitrile;
38) 6-(6-Methyl-pyridin-2-yl)-5-thieno[3,2-c]pyridin-2-yl-2,3-dihydro-1H-imidazo[1,2-a]imidazole-2-carboxylic acid amide;
39) (6-(6-Methylpyridin-2-yl)-5-(thieno[3,2-c]pyridin-2-yl)-2,3-dihydro-1H-imidazo[1,2-a]imidazol-2-yl)methanamine;
40) N-((6-(6-Methylpyridin-2-yl)-5-(thieno[3,2-c]pyridin-2-yl)-2,3-dihydro-1H-imidazo[1,2-a]imidazol-2-yl) methyl)acetamide; and
41) 6-(6-Methylpyridin-2-yl)-5-(thieno[3,2-c]pyridin-2-yl)-2,3-dihydroimidazo[2,1-b]oxazole.

The inventive compound of formula (I) typically is small organic molecules (non-peptide small molecules), having a molecular weight of less than about 1,000 daltons, preferably less than about 750 daltons, more preferably less than about 500 daltons, and even more preferably less than about 300 daltons.

The inventive compound of formula (I) may also be supplied in the form of a "prodrug" which is designed to release the compound of formula (I) when administered to a subject. Prodrug designs are well known in the art, and in the present invention, they depend on the nature of the substituents of the compounds of formula (I). For example, a substituent containing hydroxyl groups could be coupled to a carrier which renders the compound biologically inactive until the carrier is removed by endogenous enzymes or by enzymes targeted to a particular receptor or a specific location in the subject.

The inventive compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglucamine. The inventive compound of formula (I) can be treated with an acid to form acid addition salts. Examples of such an acid include hydrochloric acid, hydrobromic acid, hydroiodic acid, sulfuric acid, methanesulfonic acid, phosphoric acid, p-bromophenylsulfonic acid, carbonic acid, succinic acid, citric acid, benzoic acid, oxalic acid, malonic acid, salicylic acid, malic acid, fumaric acid, ascorbic acid, maleic acid, acetic acid, and other mineral and organic acids well known to those skilled in the art. The acid addition salts can be prepared by treating the compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute solution of a base (e.g., sodium hydroxide, sodium bicarbonate, potassium carbonate, and ammonia).

Some of the compounds of the present invention may be crystallized or recrystallized from solvents such as aqueous and organic solvents. In such cases solvates may be formed. The present invention includes within its scope stoichiometric solvates including hydrates as well as compounds containing variable amounts of water that may be produced by processes such as lyophilization.

The inventive compound of formula (I) may contain one or more asymmetric centers and thus can exist as enantiomers or diastereomers. It is to be understood that the invention includes both mixtures and separate individual isomers of the compound of formula (I). Furthermore, certain compounds of formula (I) which contain alkenyl groups may exist as cis- or trans-isomers. In such instance, the invention includes both mixtures and separate individual isomers.

The inventive compound of formula (I) may also exist in tautomeric forms and the invention includes both mixtures and separate individual tautomers thereof.

Also included in the invention are radiolabelled derivatives of the compound of formula (I) which are suitable for biological studies.

As used herein, the term "alkyl" group refers to a saturated aliphatic hydrocarbon group containing 1 to 10 (e.g., 1 to 6 or 1 to 4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as alkoxy, cycloalkoxy, amino, nitro, carboxy, cyano, halo, hydroxy, sulfo, and mercapto.

As used herein, the term "cycloalkyl" group refers to an aliphatic carbocyclic ring having 3 to 10 (e.g., 4 to 8) ring carbon atoms. Examples of a cycloalkyl group include cyclopropyl, cyclopentyl, cyclohexyl, cycloheptyl, adamantly, norbornyl, cubyl, octahydroindenyl, decahydronaphthyl, bicyclo[3.2.1]octyl, bicyclo[2.2.2]octyl, bicyclo[3.3.1]nonyl, and bicyclo[3.2.3]nonyl.

As used herein, the term "haloalkyl" group refers to an alkyl group containing one or more halogen atoms. Examples of a haloalkyl group include fluoromethyl, chloromethyl, bromomethyl, and trifluoromethyl.

As used herein, the term "halogen" or "halo" group refers to fluorine, chlorine, bromine, or iodine.

As used herein, the term "heteroaryl" group refers to a monocyclic, bicyclic, or tricyclic ring structure having 5 to 15 ring atoms, at least one of which is a heteroatom (e.g., N, O, or S) and at least one ring thereof is aromatic. Examples of a heteroaryl group is pyrazolyl, pyridyl, furyl, pyrrolyl, thienyl, thiazolyl, oxazolyl, imidazolyl, indolyl, tetrazolyl, benzofuryl, benzothiazolyl, xanthenes, thioxanthene, phenothiazine, dihydroindole, and benzo[1,3]dioxole.

As used herein, the term "heterocycle" refers to a three to seven-membered ring containing one or more heteroatomic moieties selected from S, SO, $SO_2$, O, N, or N-oxide, optionally substituted with one or more substituents selected from the group which includes substituted $C_{1-6}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

As used herein, the term "ALK5 and/or ALK4 inhibitor" refers to a compound, other than inhibitory Smads (e.g., Smad6 and Smad7), which selectively inhibits the ALK5 and/or ALK4 receptors, preferentially over p38 or type II receptors.

As used herein, the term "ALK5- and/or ALK4-mediated disease" refers to any disease which is mediated (or modulated) by ALK5 and/or ALK4, for example, a disease which is modulated by the inhibition of the phosphorylation of Smad2 and Smad3 in the TGF-β and/or activin signaling pathways.

As used herein, the term "ulcers" is used to include, but not to be limited to, diabetic ulcers, chronic ulcers, gastric ulcers, and duodenal ulcers.

The inventive compound of formula (I) may be prepared by a number of methods from commercially available or known starting materials. If the starting materials are unavailable from a commercial source, they can be prepared by procedures known in the art.

The compound of formula (I) may preferably be prepared according to the procedure shown in Reaction Scheme 1: a compound of formula (II) is subjected to bromination using bromine, followed by coupling the brominated product with a compound of formula (III) in the presence of a base in a suitable solvent. The base employable in the reaction is, but not limited to, sodium carbonate, potassium carbonate, or cesium carbonate, and the solvent employable in the reaction is, but not limited to, tetrahydrofuran, dimethylformamide, or acetonitrile.

<Reaction Scheme 1>

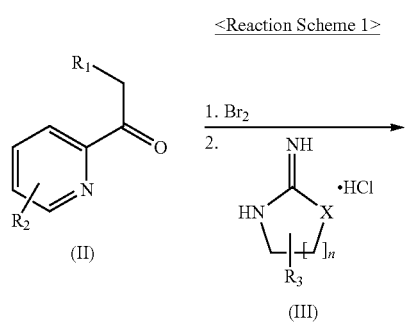

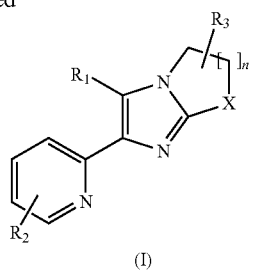

wherein,
$R_1$, $R_2$, $R_3$, n and X have the same meanings as defined above.

In another method, the compound of formula (I) may be prepared according to the procedure shown in Reaction Scheme 2: a compound of formula (IV) is subjected to a cyclization reaction with a compound of formula (V) or a compound of formula (VI) in the presence of a base in a suitable solvent. The base employable in the reaction is, but not limited to, sodium carbonate, potassium carbonate, or cesium carbonate, and the solvent employable in the reaction is, but not limited to, tetrahydrofuran, dimethylformamide, or acetonitrile.

<Reaction Scheme 2>

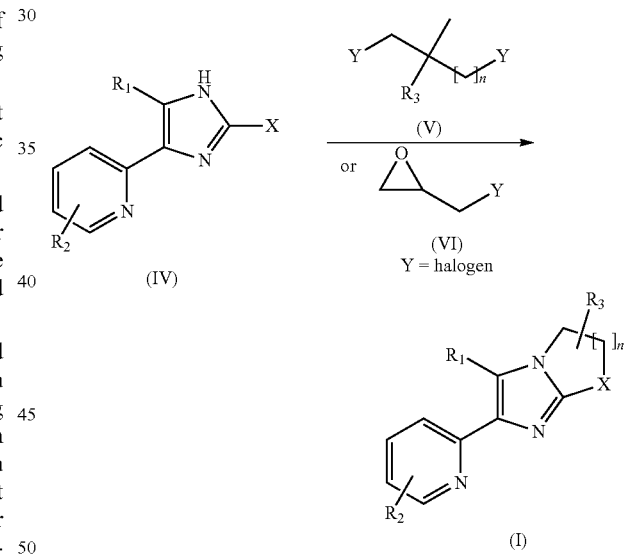

wherein,
$R_1$, $R_2$, $R_3$, n and X have the same meanings as defined above.

The compound of formula (I) may also be prepared according to the procedure shown in Reaction Scheme 3. As shown in Reaction Scheme 3, a compound of formula (VII) may be subjected to a cyclization reaction with a compound of formula (V) or a compound of formula (VI) in the presence of a base in a suitable solvent, followed by treating the cyclized product with a suitable halogenating agent to obtain a compound of formula (VIII), which may then be coupled with a borate ester, boronic acid, or tin compound using Suzuki or Stille coupling method to obtain the compound of formula (I). The base employable in the reaction is, but not limited to, sodium carbonate, potassium carbonate, or cesium carbonate, and the solvent employable in the reaction is, but not limited to, tetrahydrofuran, dimethylformamide, or acetonitrile.

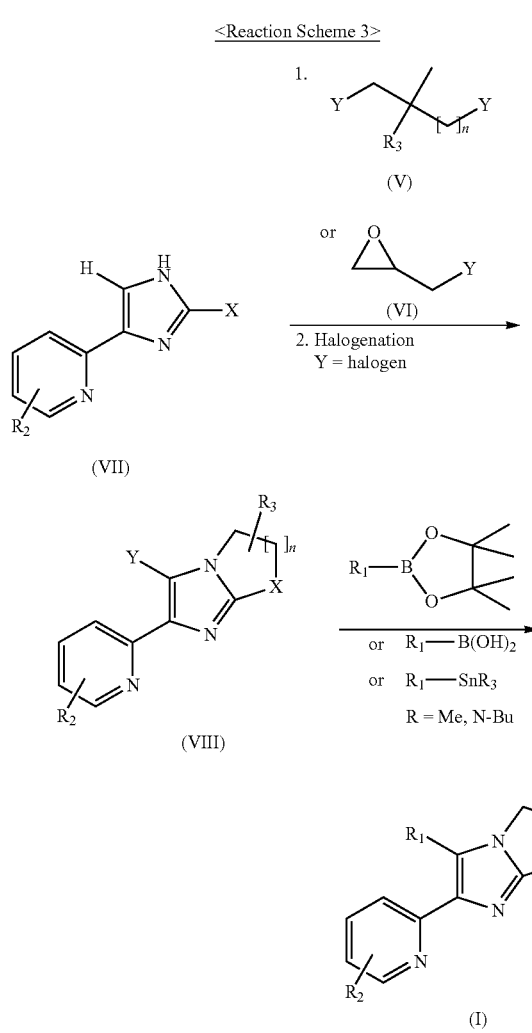

wherein,

R₁, R₂, R₃, n and X have the same meanings as defined above.

Further, the compound of formula (I) wherein X is NH may be prepared by a conventional hydrolysis method as shown in Reaction Scheme 4.

wherein, $R_1$, $R_2$, $R_3$ and n have the same meanings as defined above.

The specific substituents of the synthetic intermediates and final products shown in the above Reaction Schemes can be present in their fully elaborated forms, in protected forms with suitable protecting groups when required as one skilled in the art, or in precursor forms which can later be converted into their final forms by methods familiar to one skilled in the art. The substituents can also be added at various stages throughout the synthetic sequence or after completion of the synthetic sequence. In many cases, commonly used functional group manipulation techinques can be used to transform one intermediate into another intermediate or one compound of formula (I) into another compound of formula (I). Substituents can also be added using common reactions, such as alkyation, acylation, halogenations, or oxidation. Such manipulations are well known in the art.

Further details for the preparation of the compound of formula (I) are found in Examples.

The compound of the present invention may be administered by any suitable routes, for example, by oral, buccal, sub-lingual, rectal, vaginal, nasal, topical or parenteral (including intravenous, intramuscular, subcutaneous, and intra-coronary) administration.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% by weight up to about 98% by weight of the formulation. More usually, they will form up to about 80% by weight of the formulation.

For administration to man in the curative or prophylactic treatment of the disorders identified above, oral, buccal, or sub-lingual dosages of the inventive compound of formula (I) will generally be in the range of from 50 to 5000 mg daily for an average adult patient (70 kg). Thus for a typical adult patient, individual tablets or capsules contain from 25 to 500 mg of active compound, in a suitable pharmaceutically acceptable vehicle or carrier, for administration in single or multiple doses, once or several times per day. Dosages for parenteral administration will typically be within the range of from 25 to 250 mg per single dose as required. In practice, the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of the present invention.

For human use, the inventive compound of formula (I) can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavoring or coloring agents. Such liquid preparations may be prepared with pharmaceutically acceptable additives such as suspending agent (e.g., methylcellulose, a semi-synthetic glyceride such as Witepsol® or mixtures of glycerides such as a mixture of apricot kernel oil and PEG-6 esters or mixtures of PEG-8 and caprylic/capric glycerides). The inventive compound may also be injected parenterally, for example intravenously, intramuscularly, subcutaneously or intracoronarily. For parenteral administration, the compound is best used in the form of a sterile aqueous solution which may contain other substances, for example, salts, or monosaccharides such as mannitol or glucose, to make the solution isotonic with blood.

Accordingly, the present invention provides a pharmaceutical composition for preventing or treating a disease mediated by ALK5 or ALK4 receptors, or both (ALK5- and/or ALK4-mediated diseases), which comprises the compound of formula (I) or a pharmaceutically acceptable salt or solvate thereof as an active ingredient, together with a pharmaceutically acceptable diluent or carrier.

The invention also provides a compound of formula (I), or a pharmaceutically acceptable salt or solvate thereof; or a pharmaceutical composition containing either entity, for use in therapy.

The invention further provides a use of a compound of formula (I) or a pharmaceutically acceptable salt or solvate thereof; or a pharmaceutical composition containing either entity, for the manufacture of a medicament for the treatment of a disease, mediated by the ALK5 and/or ALK4 receptors in mammals.

In the present invention, ALK5- and/or ALK4-mediated disease may include, but are not limited to, renal-, liver- or pulmonary fibrosis, glomerulonephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, acute lung injury, adult respiratory distress syndrome, idiopathic pulmonary fibrosis, chronic obstructive pulmonary disease, pulmonary fibrosis due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Alzheimer's disease, Raynaud's syndrome, fibrotic cancers, tumor metastasis growth, radiation-induced fibrosis, and thrombosis.

In addition, the present invention provides a use of the compound of formula (I), or a pharmaceutically acceptable salt or solvate thereof for the manufacture of a medicament for preventing or treating a disease mediated by the ALK5 and/or ALK4 receptors.

The invention further provides a method of preventing or treating a disease mediated by the ALK5 and/or ALK4 receptors in a mammal, which comprises administering the compound of formula (I) or a pharmaceutically acceptable salt or solvate thereof to the mammal in need thereof. The mammal is preferably human.

The invention further provides a method for inhibiting the TGF-β and/or activin signaling pathways in mammals, for example, inhibiting the phosphorylation of Smad2 or Smad3 by ALK5 and/or ALK4.

The invention further provides a method of reducing the accumulation of excess extracellular matrix in mammals by inhibiting the TGF-β and/or activin signaling pathways, for example, inhibiting the phosphorylation of Smad2 or Smad3 by ALK5 and/or ALK4.

The invention further provides a method of inhibiting metastasis of tumor cells in mammals by inhibiting the TGF-β signaling pathway.

The invention further provides a method of treating carcinomas mediated by an overexpression of TGF-β in mammals by inhibiting the TGF-β signaling pathway.

The present invention is further described and illustrated in examples provided below, which are, however, not intended to limit the scope of the present invention.

Intermediate 1: Preparation of 2-tributylstannanyl-thieno[3,2-c]pyridine

Butyl lithium (BuLi) (1.6M in hexane, 1.4 mL) was slowly added to a stirred solution of thieno[3,2-c]pyridine (300 mg, 2.22 mmol) and tetramethylethylenediamine (335 mL, 2.22 mmol) in tetrahydrofuran (THF, 7.5 mL) at −78° C. After 15 minutes, tributyltin chloride (599 mL, 2.22 mmol) was added to the resulting mixture and stirred for 2 hours. The reaction mixture was poured into water, and the resulting solution was extracted twice with ethyl acetate (EtOAc). The combined organic layer was dried over $Na_2SO_4$, filtered, and concentrated under a reduced pressure. The residue was purified by medium pressure chromatography (MPLC) on silica gel eluting with EtOAC/hexane (1/2) to obtain the title compound (453.7 mg, 48%) as an oil.

$^1$H NMR (300 MHz, $CDCl_3$) δ 9.13 (d, 1H), 8.38 (d, 1H), 7.81 (d, 1H), 7.50 (m, 1H), 1.59 (m, 6H), 1.37 (m, 6H), 1.20 (m, 6H), 0.92 (t, 9H).

Intermediate 2: Preparation of 6-(4,4,5,5-tetramethyl-[1,3,2]dioxaborolan-2-yl)-benzothiazole

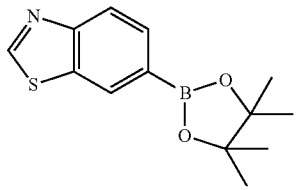 [SMILES: CC1(C)OB(c2ccc3ncsc3c2)OC1(C)C]

A suspension of 6-bromo-benzothiazole (300 mg, 1.40 mmol), bis(pinacolato)diboron (427 mg, 1.68 mmol) and potassium acetate (KOAc)(412 mL, 4.20 mmol) in N,N-dimethylformamide (DMF, 6 mL) was added to PdCl$_2$ (dppf)$_2$ (57 mg, 0.07 mmol), and the mixture was stirred at 100° C. under N$_2$ for 4 hours. After cooling to room temperature, the mixture was diluted with brine and EtOAc, and stirred for 5 minutes. After separating the organic layer, the aqueous layer was extracted three times with EtOAc. The organic layers were combined, dried over Na$_2$SO$_4$, filtered, and concentrated under a reduced pressure. The residue was purified by MPLC on silica gel eluting with EtOAC/hexane (1/20) to obtain the title compound (329 mg, 90%) as a white solid.

$^1$H NMR (300 MHz, CDCl$_3$) δ 9.06 (s, 1H), 8.46 (s, 1H), 8.13 (d, 1H), 7.94 (d, 1H), 1.38 (s, 12H).

Intermediate 3: Preparation of 2-benzoibithiophen-5-yl-4,4,5,5-tetramethyl-[1,3,2]dioxaborolane

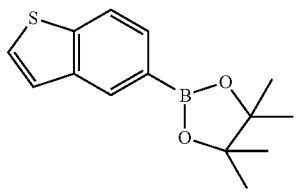 [SMILES: CC1(C)OB(c2ccc3sccc3c2)OC1(C)C]

The procedure described for Intermediate 2 was repeated except that 5-bromo-benzo[b]thiophene (300 mg, 1.41 mmol) was used instead of 6-bromo-benzothiazole to obtain the title compound (290 mg, 79%) as a pale blue solid.

$^1$H NMR (300 MHz, CDCl$_3$) δ 8.31 (s, 1H), 7.88 (d, 1H), 7.74 (d, 1H), 7.41 (d, 1H), 7.34 (d, 1H), 1.37 (s, 12H).

Intermediate 4: Preparation of 6-(4,4,5,5-tetramethyl-[1,3,2]dioxaborolan-2-yl)-[1,2,4]triazolo[1,5-a]pyridine

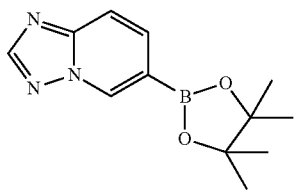 [SMILES: CC1(C)OB(c2ccc3ncnn3c2)OC1(C)C]

The procedure described for Intermediate 2 was repeated except that 6-Iiodo-[1,2,4]triazolo[1,5-a]pyridine (1.0 g, 4.08 mmol) was used instead of 6-bromo-benzothiazole and MPLC on silica gel elution was conducted with EtOAC/hexane (1/2) to obtain the title compound (645.4 mg, 65%) as a white solid.

$^1$H NMR (300 MHz, CDCl$_3$) δ 8.95 (s, 1H), 8.35 (s, 1H), 7.81 (d, 1H), 7.72 (d, 1H), 1.36 (s, 12H).

Intermediate 5: Preparation of 5-(4,4,5,5-tetramethyl-[1,3,2]dioxaborolan-2-yl)-benzoxazole

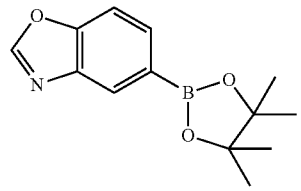 [SMILES: CC1(C)OB(c2ccc3ocnc3c2)OC1(C)C]

The procedure described for Intermediate 2 was repeated except that 5-bromo-benzoxazole (200 mg, 1.01 mmol) was used instead of 6-bromo-benzothiazole and MPLC on silica gel elution was conducted with EtOAC/hexane (1/2) to obtain the title compound (222.4 mg, 90%) as a yellow solid.

$^1$H NMR (300 MHz, CDCl$_3$) δ 8.25 (s, 1H), 8.09 (s, 1H), 7.85 (d, 1H), 7.58 (d, 1H), 1.37 (s, 12H).

Intermediate 6: Preparation of 4-(4,4,5,5-tetramethyl-[1,3,2]dioxaborolan-2-yl)-quinoline

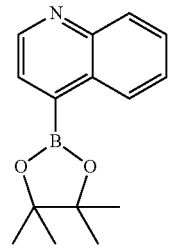 [SMILES: CC1(C)OB(c2ccnc3ccccc23)OC1(C)C]

The procedure described for Intermediate 2 was repeated except that 4-bromo-quinoline (300 mg, 1.44 mmol) was used instead of 6-bromo-benzothiazole and MPLC on silica gel elution was conducted with EtOAC/CH$_2$Cl$_2$ (1/1) to obtain the title compound (110 mg, 30%) as a pale brown solid.

$^1$H NMR (300 MHz, CDCl$_3$) δ 8.93 (d, 1H), 8.64 (dd, 1H), 8.11 (dd, 1H), 7.85 (d, 1H), 7.71 (m, 1H), 7.58 (m, 1H), 1.44 (s, 12H).

Intermediate 7: Preparation of 5-(4,4,5,5-tetramethyl-[1,3,2]dioxaborolan-2-yl)-benzo[1,3]dioxole

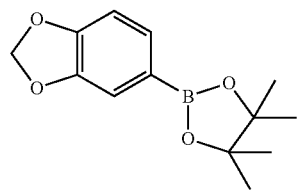 [SMILES: CC1(C)OB(c2ccc3c(c2)OCO3)OC1(C)C]

The procedure described for Intermediate 2 was repeated except that 5-bromo-benzo[1,3]dioxole (200 mg, 0.99 mmol) was used instead of 6-bromo-benzothiazole to obtain the title compound (220 mg, 90%) as a pale yellow oil.

¹H NMR (300 MHz, CDCl₃) δ 7.35 (d, 1H), 7.23 (s, 1H), 6.82 (d, 1H), 5.95 (s, 2H), 1.32 (s, 12H).

Intermediate 8: Preparation of 6-(4,4,5,5-tetramethyl-[1,3,2]dioxaborolan-2-yl)-2,3-dihydro-benzo[1,4]dioxine

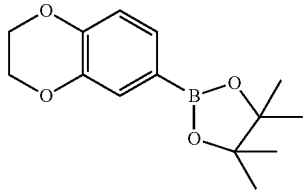 [SMILES: CC1(C)OB(c2ccc3c(c2)OCCO3)OC1(C)C]

The procedure described for Intermediate 2 was repeated except that 6-bromo-2,3-dihydro-benzo[1,4]dioxine (400 mg, 1.86 mmol) was used instead of 6-bromo-benzothiazole to obtain the title compound (431 mg, 88%) as a pale yellow oil.

¹H NMR (300 MHz, CDCl₃) δ 7.31 (d, 1H), 7.29 (dd, 1H), 6.85 (d, 1H), 4.22 (m, 4H), 1.31 (s, 12H).

Intermediate 9: Preparation of 2-imidazol-1-yl-7-(4,4,5,5-tetramethyl-[1,3,2]dioxaborolan-2-yl)-quinoxaline

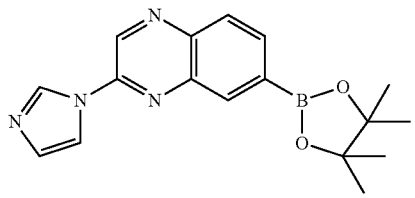 [SMILES: CC1(C)OB(c2ccc3ncc(-n4ccnc4)nc3c2)OC1(C)C]

The procedure described for Intermediate 2 was repeated except that 7-bromo-2-imidazol-1-yl-quinoxaline (225 mg, 0.82 mmol) was used instead of 6-bromo-benzothiazole and MPLC on silica gel elution was conducted with 1% MeOH in CH₂Cl₂ to obtain the title compound (130 mg, 94%) as a brown oil.

¹H NMR (300 MHz, CDCl₃) δ 9.10 (s, 1H), 8.56 (d, 1H), 8.12 (s, 1H), 8.10 (dd, 1H), 7.89 (s, 1H), 7.81 (dd, 1H), 7.31 (s, 1H), 1.41 (s, 12H).

Intermediate 10: Preparation of 2-pyrazol-1-yl-7-(4,4,5,5-tetramethyl-[1,3,2]dioxaborolan-2-yl)-quinoxaline

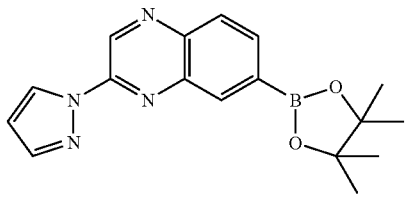 [SMILES: CC1(C)OB(c2ccc3ncc(-n4cccn4)nc3c2)OC1(C)C]

The procedure described for Intermediate 2 was repeated except that 7-bromo-2-pyrazol-1-yl-quinoxaline (200 mg, 0.73 mmol) was used instead of 6-bromo-benzothiazole and MPLC on silica gel elution was conducted with EtOAC/hexane (1/10) to obtain the title compound (220 mg, 94%) as a brown solid.

¹H NMR (300 MHz, CDCl₃) δ 9.71 (s, 1H), 8.70 (d, 1H), 8.51 (s, 1H), 8.08 (d, 1H), 8.08 (d, 1H), 7.85 (d, 1H), 6.57 (dd, 1H), 1.41 (s, 12H).

Intermediate 11: Preparation of 1-[6-(6-methyl-pyridin-2-yl)-2,3-dihydro-imidazo[1,2-a]imidazol-1-yl]-ethanone

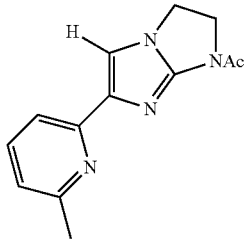

A solution of 1-(6-methyl-pyridin-2-yl)-ethanone (5.31 g, 39.3 mmol) and 33% hydrobromic acid (HBr)/acetic acid (AcOH)(6.9 mL, 69.3 mmol) was added slowly to bromine (2 mL, 39.3 mmol), and the reaction mixture was stirred for 1 hour. The mixture was concentrated under a reduced pressure, diluted with toluene, and concentrated under a reduced pressure to obtain 2-bromo-1-(6-methyl-pyridin-2-yl)-ethanone hydrobromide (12.14 g, 105%). The bromide (10 g, 32.4 mmol) thus obtained was dissolved in water and CH₂Cl₂ and then neutralized with NaHCO₃ solution. The mixture was extracted three times with CH₂Cl₂, dried over anhydrous MgSO₄, filtered and evaporated to dryness under a reduced pressure. The residue was dissolved in DMF (90 mL), and N-acetyl-guanidine (9.7 g, 95.9 mmol) was added thereto. After stirring for 64 hours, the mixture was concentrated under a reduced pressure. The residue was diluted with water, extracted twice with MeOH and CH₂Cl₂, dried over anhydrous MgSO₄, filtered and evaporated to form a solid under a reduced pressure. The mixture was diluted with CH₂Cl₂, filtered and washed with EtOAc/hexane (1/1) to obtain N-[5-(6-methyl-pyridin-2-yl)-1H-imidazol-2-yl]-acetamide (2.29 g, 32%) as a white solid. The filtrate was further purified by MPLC on NH silica gel eluting with 1% MeOH/CH₂Cl₂ to obtain the above compound (548 mg, 5.7%).

1,2-Dibromoethane (2.7 mL, 31.8 mmol) was added to a mixture of the above compound (2.29 g, 10.6 mmol) and Cs₂CO₃ (17 g, 53.0 mmol) in DMF (130 mL) at 80° C., and the reaction mixture was stirred for 5 hours. After cooling to room temperature, the mixture was filtered through celite, washed with DMF, and concentrated under a reduced pressure. The residue was diluted with water, extracted three times with CH₂Cl₂, dried over anhydrous MgSO₄, filtered and evaporated under a reduced pressure. The residue was purified by MPLC on NH silica gel eluting with CH₂Cl₂/hexane/EtOAc (3/1/0.5→3/0/1) to obtain the title compound (1.27 g, 49%) as a white solid.

¹H NMR (300 MHz, CDCl₃) δ 7.68 (d, 1H), 7.57 (t, 1H), 7.46 (s, 1H), 6.98 (d, 1H), 4.46 (m, 2H), 4.15 (m, 2H), 2.70 (s, 3H), 2.54 (s, 3H).

Intermediate 12: Preparation of 1-[5-bromo-6-(6-methyl-pyridin-2-yl)-2,3-dihydro-imidazo[1,2-a]imidazol-1-yl]-ethanone

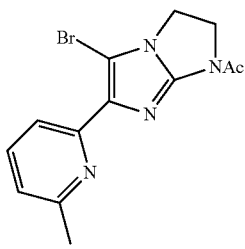

To a stirred solution of 1-[6-(6-methyl-pyridin-2-yl)-2,3-dihydro-imidazo[1,2-a]imidazol-1-yl]-ethanone (Intermediate 11, 1.27 g, 5.22 mmol) in dry $CH_2Cl_2$ (50 mL) at 0° C. was added N-bromosuccinimide (929 mg, 5.22 mmol) portionwise and the mixture was stirred for 20 minutes. The reaction mixture was diluted with water, extracted three times with $CH_2Cl_2$, dried over anhydrous $MgSO_4$, filtered and evaporated under a reduced pressure. The residue was purified by MPLC on NH silica gel eluting with $CH_2Cl_2$/hexane/EtOAc (3/1/0.5→3/1/1) to obtain the title compound (1.62 g, 96%) as a white solid.

$^1$H NMR (300 MHz, $CDCl_3$) δ 7.68 (d, 1H), 7.59 (t, 1H), 7.03 (d, 1H), 4.48 (m, 2H), 4.12 (m, 2H), 2.67 (s, 3H), 2.60 (s, 3H).

Intermediate 13: Preparation of 2-(2-(benzylsulfonyl)-1H-imidazol-4-yl)-6-methylpyridine

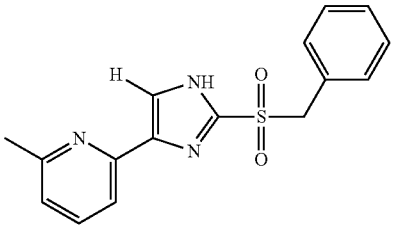 [SMILES: Cc1cccc(-c2c[nH]c(S(=O)(=O)Cc3ccccc3)n2)n1]

Benzyl bromide (1.71 g, 10 mmol) was added to a mixture of thiourea (761 mg, 10 mmol) in isopropyl alcohol (30 mL), and the mixture was stirred at 85° C. for 1 hour. After cooling to room temperature, the mixture was concentrated under a reduced pressure, diluted with toluene, and concentrated under a reduced pressure to obtain benzyl carbamimidothioate hydrobromide (2.48 g, 100%) as a white solid. 2-bromo-1-(6-methyl-pyridin-2-yl)-ethanone hydrobromide (see the procedure described for Intermediate 11, 294 mg, 1 mmol) was added to a mixture of the above compound (741 mg, 3 mmol) and $Na_2CO_3$ (435 mg, 4.1 mmol) in DMF (3 mL) at 50° C., and the mixture was stirred for 16 hours. After cooling to room temperature, the mixture was diluted with brine and $CH_2Cl_2$, and stirred for 5 minutes. After separating organic layer, the aqueous layer was extracted three times with $CH_2Cl_2$, dried over $Na_2SO_4$, filtered, and concentrated under a reduced pressure. The residue was purified by MPLC on NH silica gel eluting with $EtOAC/CH_2Cl_2$ (0%→20%) to obtain 2-(2-(benzylthio)-1H-imidazol-4-yl)-6-methylpyridine (177 mg, 63%) as a pale yellow oil. To a stirred solution of the oil (177 mg, 0.63 mmol) in dry $CH_2Cl_2$ at 0° C. was added 3-chloroperbenzoic acid (310 mg, 1.38 mmol) and the mixture was stirred for 1 hour. The mixture was diluted with $H_2O$ and $CH_2Cl_2$ and then stirred for 5 minutes. After separating organic layer, the aqueous layer was extracted twice with $CH_2Cl_2$. The organic layers were combined, dried over $Na_2SO_4$, filtered and concentrated under a reduced pressure. The residue was purified by MPLC on NH silica gel eluting with $MeOH/CH_2Cl_2$ (5%) to obtain the title compound (113 mg, 58%) as a white oil.

MS (ESI) m/z 314.05 (MH$^+$).

$^1$H NMR (300 MHz, $CDCl_3$) δ 7.64 (m, 2H), 7.26 (m, 3H), 7.16 (m, 3H), 7.06 (d, 1H), 4.61 (s, 2H), 2.50 (s, 3H).

Intermediate 14: Preparation of 5-bromo-6-(6-methylpyridin-2-yl)-2,3-dihydroimidazo[2,1-b]oxazole

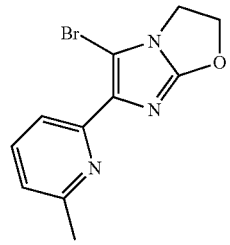 [SMILES: Cc1cccc(-c2nc3n(c2Br)CCO3)n1]

2-Bromoethanol (135 µL, 1.92 mmol) was added to a mixture of 2-(2-(benzylsulfonyl)-1H-imidazol-4-yl)-6-methylpyridine (Intermediate 13, 200 mg, 0.64 mmol) and $Cs_2CO_3$ (831 mg, 2.56 mmol) in DMF (4 mL) at 80° C., and the reaction mixture was stirred for 4 hours. After cooling to room temperature, the mixture was diluted with saturated $NH_4Cl$ solution and $CH_2Cl_2$ and stirred for 5 minutes. After separating organic layer, the aqueous layer was extracted twice with $CH_2Cl_2$. The organic layers were combined, dried over $Na_2SO_4$, filtered, and concentrated under a reduced pressure. The residue was purified by MPLC on NH silica gel eluting with $EtOAC/CH_2Cl_2$ (0%→30%) to obtain 2-(2-(benzylsulfonyl)-4-(6-methylpyridin-2-yl)-1H-imidazol-1-yl)ethanol (130 mg, 57%) as a white foam. Sodium hydride (14.5 mg, 0.36 mmol) was added to a solution of the above compound (130 mg, 0.36 mmol) in dry THF (6 mL) at room temperature and the mixture was stirred for 2 hours. The mixture was diluted with $H_2O$ and EtOAC, and stirred for 5 minutes. After separating organic layer, the aqueous layer was extracted twice with $MeOH/CH_2Cl_2$ (3%). The combined organic layer was dried over $Na_2SO_4$, filtered, and concentrated under a reduced pressure. The residue was purified by MPLC on NH silica gel eluting with $EtOAC/CH_2Cl_2$ (0%→10%) to obtain 6-(6-methylpyridin-2-yl)-2,3-dihydroimidazo[2,1-b]oxazole (54 mg, 74%) as a white solid. The resulting compound was then reacted as described in Intermediate 12 to afford after MPLC on NH silica gel eluting with $CH_2Cl_2$/hexane (50%→100%), the title compound (35 mg, 42%) as a pale brown solid.

$^1$H NMR (300 MHz, $CDCl_3$) δ 7.64 (d, 1H), 7.56 (t, 1H), 7.00 (dd, 1H), 5.03 (dd, 2H), 4.18 (dd, 2H), 2.58 (s, 3H).

Intermediate 15: Preparation of 1-acetyl-6-(6-methyl-pyridin-2-yl)-2,3-dihydro-1H-imidazoil[1,2-a]imidazole-2-carboxylic acid ethyl ester

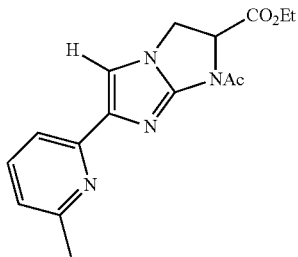

The procedure described for Intermediate 11 was repeated except that N-[5-(6-methyl-pyridin-2-yl)-1H-imidazol-2-yl]-acetamide (see Intermediate 11, 500 mg, 2.31 mmol) and 2,3-dibromo-propionic acid ethyl ester (1 mL, 6.93 mmol) were used instead of 1,2-dibromoethane, and MPLC on NH silica gel elution was conducted with $CH_2Cl_2$/EtOAC/hexane (3/0.5/1) to obtain the title compound (577.4 mg, 79%) as a brown oil.

$^1$H NMR (300 MHz, $CDCl_3$) δ 7.69 (d, 1H), 7.57 (t, 1H), 7.42 (s, 1H), 6.97 (d, 1H), 5.36 (dd, 1H), 4.40 (t, 2H), 4.25 (q, 2H), 4.14 (dd, 2H), 2.73 (s, 3H), 2.53 (s, 3H), 1.28 (t, 3H).

Intermediate 16: Preparation of 1-acetyl-5-bromo-6-(6-methyl-pyridin-2-yl)-2,3-dihydro-1H-imidazo[1,2-a]imidazole-2-carboxylic acid ethyl ester

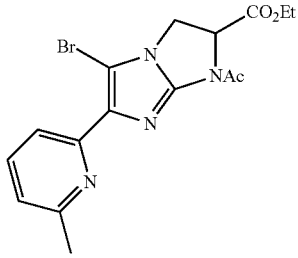

The procedure described for Intermediate 12 was repeated except that 1-acetyl-6-(6-methyl-pyridin-2-yl)-2,3-dihydro-1H-imidazo[1,2-a]imidazole-2-carboxylic acid ethyl ester (Intermediate 15, 577.4 mg, 1.83 mmol) was used instead of 1-[6-(6-methyl-pyridin-2-yl)-2,3-dihydro-imidazo[1,2-a]imidazol-1-yl]-ethanone (Intermediate 11). The crude compound was purified by recrystallization from $CH_2Cl_2$/MeOH/hexane to obtain the title compound (414.7 mg, 57%) as a white solid.

$^1$H NMR (300 MHz, $CDCl_3$) δ 7.68 (d, 1H), 7.59 (t, 1H), 7.03 (d, 1H), 5.37 (dd, 1H), 4.35 (t, 2H), 4.27 (q, 2H), 4.12 (dd, 2H), 2.71 (s, 3H), 2.59 (s, 3H), 1.30 (t, 3H).

Intermediate 17: Preparation of 1-acetyl-6-(6-methyl-pyridin-2-yl)-2,3-dihydro-1H-imidazo[1,2-a]imidazole-2-carbonitrile

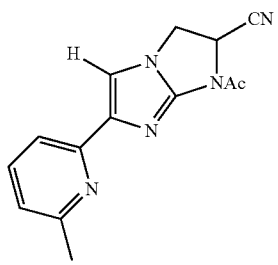

The procedure described for Intermediate 11 was repeated except that N-[5-(6-methyl-pyridin-2-yl)-1H-imidazol-2-yl]-acetamide (see the procedure described for Intermediate 11, 500 mg, 2.31 mmol) and 2,3-dibromo-propionic acid ethyl ester (762 μL, 6.93 mmol) were used instead of 1,2-dibromoethane, and MPLC on NH silica gel elution was conducted with $CH_2Cl_2$/EtOAC/hexane (3/0.5/1) to obtain the title compound (345.8 mg, 56%) as a pale brown foam.

$^1$H NMR (300 MHz, $CDCl_3$) δ 7.67 (d, 1H), 7.59 (t, 1H), 7.49 (s, 1H), 7.01 (d, 1H), 5.61 (dd, 1H), 4.47 (m, 2H), 2.74 (s, 3H), 2.54 (s, 3H).

Intermediate 18: Preparation of 1-acetyl-5-bromo-6-(6-methyl-pyridin-2-yl)-2,3-dihydro-1H-imidazo[1,2-a]imidazole-2-carbonitrile

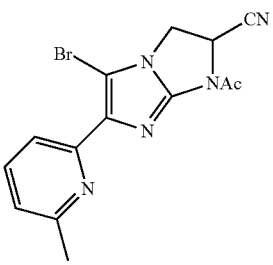

The procedure described for Intermediate 12 was repeated except that 1-acetyl-6-(6-methyl-pyridin-2-yl)-2,3-dihydro-1H-imidazo[1,2-a]imidazole-2-carbonitrile (Intermediate 17, 577.4 mg, 1.83 mmol) was used instead of 1-[6-(6-methyl-pyridin-2-yl)-2,3-dihydro-imidazo[1,2-a]imidazol-1-yl]-ethanone (Intermediate 11). The crude compound was purified by recrystallization from $CH_2Cl_2$/MeOH/hexane to obtain the title compound (240 mg, 53%) as a white solid.

$^1$H NMR (300 MHz, $CDCl_3$) δ 7.63 (d, 1H), 7.59 (t, 1H), 7.04 (dd, 1H), 5.61 (dd, 1H), 4.40 (m, 2H), 2.70 (s, 3H), 2.56 (s, 3H).

Example 1: Preparation of 1-[6-(6-methyl-pyridin-2-yl)-5-quinoxalin-6-yl-2,3-dihydro-imidazo[1,2-a]imidazol-1-yl]-ethanone

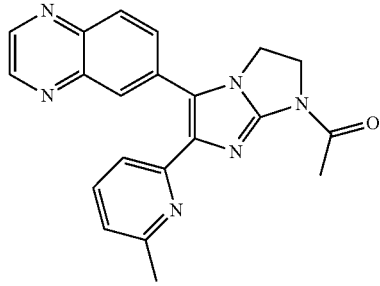 [SMILES: CC(=O)N1CCn2c1nc(-c1cccc(C)n1)c2-c1ccc2nccnc2c1]

1,2-Dibromoethane (56 μL, 0.65 mmol) was added to a mixture of N-[5-(6-methyl-pyridin-2-yl)-4-quinoxalin-6-yl-1H-imidazol-2-yl]-acetamide (150 mg, 0.44 mmol) and K$_2$CO$_3$ (304 mg, 2.20 mmol) in CH$_3$CN (6 mL) at 80° C. 1,2-dibromoethane (25 μL, 0.29 mmol) was added thereto in three portions every 2 hours, and the reaction mixture was stirred for 15 hours. After cooling to room temperature, the mixture was filtered through celite, washed with CH$_2$Cl$_2$, and concentrated under a reduced pressure. The residue was purified by MPLC on NH silica gel eluting with CH$_2$Cl$_2$ to obtain the title compound (36.7 mg, 23%) as a yellow solid.

MS (ESI) m/z 371.68 (MH$^+$).

$^1$H NMR (300 MHz, CDCl$_3$) δ 8.84 (d, 2H), 8.15 (d, 1H), 8.03 (d, 1H), 7.97 (dd, 1H), 7.62 (d, 1H), 7.55 (t, 1H), 7.00 (d, 1H), 4.55 (t, 2H), 4.27 (t, 2H), 2.76 (s, 3H), 2.36 (s, 3H).

Example 2: Preparation of 6-[2-(6-methyl-pyridin-2-yl)-6,7-dihydro-5H-imidazo[1,2-a]imidazol-3-yl]-quinoxaline

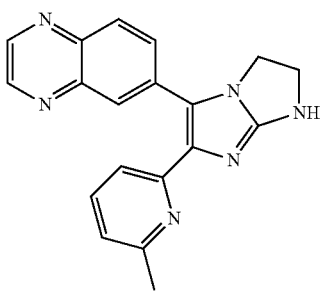 [SMILES: Cc1cccc(-c2nc3n(c2-c2ccc4nccnc4c2)CCN3)n1]

1N NaOH (97 μL, 0.097 mmol) was added to a suspension of 1-[6-(6-methyl-pyridin-2-yl)-5-quinoxalin-6-yl-2,3-dihydro-imidazo[1,2-a]imidazol-1-yl]-ethanone (Example 1, 30 mg, 0.08 mmol) in MeOH (2 mL), and the mixture was stirred at 60° C. for 2 hours. After cooling to room temperature, the reaction mixture was concentrated under a reduced pressure. The residue was purified by MPLC on NH silica gel eluting with 1% MeOH/CH$_2$Cl$_2$ to obtain the title compound (18.7 mg, 71%) as a yellow solid.

MS (ESI) m/z 329.64 (MH$^+$).

$^1$H NMR (300 MHz, CDCl$_3$) δ 8.82 (d, 1H), 8.80 (d, 1H), 8.12 (t, 1H), 7.98 (m, 2H), 7.50 (d, 1H), 7.49 (t, 1H), 6.97 (dd, 1H), 4.57 (br s, 1H), 4.24 (m, 2H), 4.09 (t, 2H), 2.39 (s, 3H).

Example 3: Preparation of 6-[2-(6-methyl-pyridin-2-yl)-5,6,7,8-tetrahydro-imidazo[1,2-a]pyrimidin-3-yl]-quinoxaline

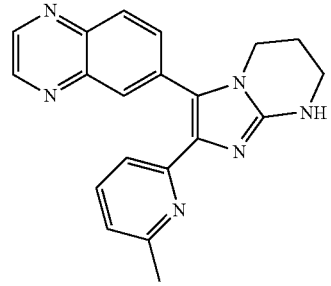 [SMILES: Cc1cccc(-c2nc3n(c2-c2ccc4nccnc4c2)CCCN3)n1]

A solution of bromine (0.117 mL, 2.28 mmol) in 1,4-dioxane (2 mL) were slowly added to a stirred solution of 1-(6-methyl-pyridin-2-yl)-2-quinoxalin-6-yl-ethanone (600 mg, 2.28 mmol) in 1,4-dioxane (10 mL) After stirring for 1 hour, the reaction mixture was partitioned between t-BuOMe and water. The organic layer was separated and the aqueous layer was neutralized with a NaHCO$_3$ solution. The organic layer was mixed with the aqueous layer and separated. The aqueous layer was extracted twice with CH$_2$Cl$_2$, dried over anhydrous Na$_2$SO$_4$, filtered and evaporated to dryness under a reduced pressure to obtain the bromide (877 mg, 112%). Tetrahydro-pyrimidin-2-ylideneamine hydrochloride (330 mg, 2.44 mmol) and K$_2$CO$_3$ (337 mg, 2.44 mmol) were added to a solution of the bromide (278 mg, 0.81 mmol) in DMF (3 mL), and the mixture was stirred at 80° C. for 5 hours. After cooling to room temperature, the reaction mixture was diluted with THF (5 mL), filtered through celite, and washed with THF. The filtrate was concentrated under a reduced pressure. The residue was purified by MPLC on NH silica gel eluting with 1% MeOH/CH$_2$Cl$_2$ and recrystallized with EtOAc/hexane to obtain the title compound (42 mg, 15%) as an orange solid.

MS (ESI) m/z 343.69 (MH$^+$).

$^1$H NMR (300 MHz, CDCl$_3$) δ 8.84 (d, 1H), 8.83 (d, 1H), 8.09 (d, 1H), 8.02 (d, 1H), 7.84 (dd, 1H), 7.40 (t, 1H), 7.27 (d, 1H), 6.90 (d, 1H), 4.97 (br s, 1H), 3.90 (t, 2H), 3.49 (m, 2H), 2.38 (s, 3H), 2.09 (quintet, 2H).

Example 4: Preparation of 6-[2-(6-methyl-pyridin-2-yl)-6,7-dihydro-5H-imidazo[1,2-a]imidazol-3-yl]-quinoline

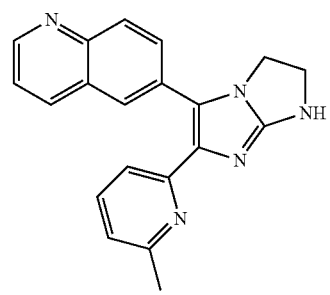 [SMILES: Cc1cccc(-c2nc3n(c2-c2ccc4ncccc4c2)CCN3)n1]

1,2-Dibromoethane (56 μL, 0.65 mmol) was added to a mixture of N-[5-(6-methyl-pyridin-2-yl)-4-quinolin-6-yl- 1H-imidazol-2-yl]-acetamide (150 mg, 0.44 mmol) and K$_2$CO$_3$ (304 mg, 2.20 mmol) in CH$_3$CN (6 mL) at 80° C. After 2.5 hours, 1,2-dibromoethane (28 μL, 0.33 mmol) was added thereto and the reaction mixture stirred for 20 hours. After cooling to room temperature, the mixture was filtered through celite, washed with CH$_2$Cl$_2$, and concentrated under a reduced pressure. The residue was purified by MPLC on NH silica gel with eluting solvent (CH$_2$Cl$_2$→10% EtOAc/CH$_2$Cl$_2$→2% MeOH/CH$_2$Cl$_2$) to obtain the cyclic compound (19.1 mg, 12%) as a pale yellow solid. 1N NaOH (62 μL, 0.062 mmol) was added to a suspension of the cyclic compound (19.1 mg, 0.052 mmol) in MeOH (2 mL), and the mixture was stirred at 60° C. for 2-hours. After cooling to room temperature, the reaction mixture was concentrated under a reduced pressure. The residue was purified by MPLC on NH silica gel eluting with 1.5% MeOH/CH$_2$Cl$_2$ to obtain the title compound (10.9 mg, 64%) as a yellow solid.

MS (ESI) m/z 329.64 (MH$^+$).

$^1$H NMR (300 MHz, CDCl$_3$) δ 8.89 (dd, 1H), 8.11 (m, 1H), 8.03 (d, 1H), 7.94 (d, 1H), 7.82 (dd, 1H), 7.45 (t, 1H), 7.41 (d, 1H), 7.39 (t, 1H), 6.92 (dd, 1H), 4.44 (br t, 1H), 4.16 (m, 2H), 4.07 (m, 2H), 2.40 (s, 3H).

Example 5: Preparation of 6-[2-(6-methyl-pyridin-2-yl)-5,6,7,8-tetrahydro-imidazo[1,2-a]pyrimidin-3-yl]-quinoline

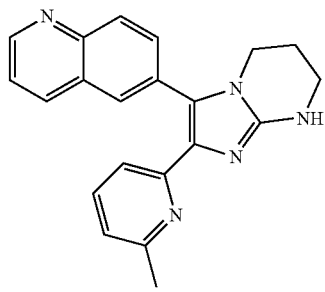 [SMILES: Cc1cccc(-c2nc3n(c2-c2ccc4ncccc4c2)CCCN3)n1]

1,3-Dibromopropane (45 μL, 0.44 mmol) was added to a mixture of N-[5-(6-methyl-pyridin-2-yl)-4-quinolin-6-yl-1H-imidazol-2-yl]-acetamide (100 mg, 0.29 mmol) and K$_2$CO$_3$ (200 mg, 1.45 mmol) in CH$_3$CN (4 mL) at 80° C. After 2.5 hours, 1,3-dibromopropane (23 μL, 0.22 mmol) was added thereto and the reaction mixture was stirred for 2.5 hours. After cooling to room temperature, the mixture was filtered through celite, washed with CH$_2$Cl$_2$, and concentrated under a reduced pressure. The residue was purified by MPLC on NH silica gel eluting with MeOH/CH$_2$Cl$_2$ (0→2%) to obtain the cyclic compound (60.4 mg, 54%) as a pale yellow solid. 1N NaOH (190 μL, 0.19 mmol) was added to a solution of the cyclic compound (60.4 mg, 0.16 mmol) in MeOH (3 mL), and the mixture was stirred at 60° C. for 1 hour. After cooling, the reaction mixture was concentrated under a reduced pressure. The residue was purified by MPLC on NH silica gel eluting with 1.5% MeOH/CH$_2$Cl$_2$ and recrystallized from EtOAc to obtain the title compound (10.1 mg, 18%) as a yellow solid.

MS (ESI) m/z 342.86 (MH$^+$).

$^1$H NMR (300 MHz, CDCl$_3$) δ 8.92 (dd, 1H), 8.13 (d, 1H), 8.08 (d, 1H), 7.86 (d, 1H), 7.73 (dd, 1H), 7.42 (dd, 1H), 7.33 (t, 1H), 7.14 (d, 1H), 6.87 (d, 1H), 4.90 (br s, 1H), 3.81 (t, 2H), 3.48 (m, 2H), 2.40 (s, 3H), 2.09 (quintet, 2H).

Example 6: Preparation of 2-[2-(6-methyl-pyridin-2-yl)-6,7-dihydro-5H-imidazo[1,2-a]imidazol-3-yl]-thieno[3,2-c]pyridine

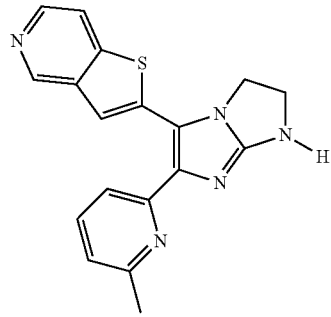 [SMILES: Cc1cccc(-c2nc3n(c2-c2cc4cnccc4s2)CCN3)n1]

1-[5-Bromo-6-(6-methyl-pyridin-2-yl)-2,3-dihydro-imidazo[1,2-a]imidazol-1-yl]-ethanone (Intermediate 12, 100 mg, 0.31 mmol), Pd(PPh$_3$)$_4$ (17.9 mg, 0.016 mmol) and CuBr (4.5 mg, 0.031 mmol) were added to a solution of 2-tributylstannanyl-thieno[3,2-c]pyridine (Intermediate 1, 158 mg, 0.37 mmol) in 1,4-dioxane (4.5 mL), and the mixture was stirred at 100° C. under N$_2$ for 14 hours. After cooling to room temperature, the mixture was filtered through celite, washed with CH$_2$Cl$_2$, and concentrated under a reduced pressure. The residue was purified by MPLC on NH silica gel eluting with CH$_2$Cl$_2$/hexane/EtOAC (3/1/0.5→3/0/1→3/0/2) to obtain the coupled compound (83.5 mg, 72%) as a yellow solid. 1N NaOH (259 μL, 0.259 mmol) was added to a suspension of the coupled compound (80.9 mg, 0.125 mmol) in MeOH (6.5 mL), and the mixture was stirred at 70° C. for 1.5 hours. After cooling to room temperature, the reaction mixture was concentrated under a reduced pressure. The residue was purified by MPLC on NH silica gel eluting with MeOH/CH$_2$Cl$_2$ (1%→2%) to obtain the title compound (61.6 mg, 86%) as a yellow solid.

MS (ESI) m/z 334.77 (MH$^+$).

$^1$H NMR (300 MHz, CDCl$_3$+CD$_3$OD) δ 8.89 (s, 1H), 8.27 (d, 1H), 7.67 (d, 1H), 7.63 (s, 1H), 7.55 (t, 1H), 7.43 (d, 1H), 7.02 (d, 1H), 4.26 (m, 2H), 4.04 (m, 2H), 2.52 (s, 3H).

Example 7: Preparation of 6-[2-(6-methyl-pyridin-2-yl)-6,7-dihydro-5H-imidazo[1,2-a]imidazol-3-yl]-benzothiazole

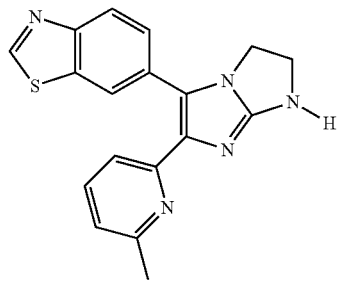 [SMILES: Cc1cccc(-c2nc3n(c2-c2ccc4ncsc4c2)CCN3)n1]

Pd(PPh$_3$)$_4$ (17.9 mg, 0.016 mmol) was added to a mixture of 6-(4,4,5,5-tetramethyl-[1,3,2]dioxaborolan-2-yl)-benzothiazole (Intermediate 2, 97.0 mg, 0.37 mmol), 1-[5-bromo-6-(6-methyl-pyridin-2-yl)-2,3-dihydro-imidazo[1,2-a]imidazol-1-yl]-ethanone (Intermediate 12, 100 mg, 0.31 mmol), K₂CO₃ (85.7 mg, 0.62 mmol) in toluene (4.5 mL) and EtOH (0.23 mL), and the mixture was stirred at 100° C. under N₂ for 13 hours. After cooling to room temperature, the mixture was filtered through celite, washed with CH₂Cl₂, and concentrated under a reduced pressure. The residue was purified by MPLC on NH silica gel eluting with CH₂Cl₂/hexane/EtOAC (3/1/0.5→3/1/1) and recrysallization from CH₂Cl₂/hexane to obtain the coupled compound (49.2 mg, 42%) as a white solid. To a suspension of the above compound (49.2 mg, 0.049 mmol) in MeOH (4.5 mL) was added 1N NaOH (170 µL, 0.17 mmol) and the mixture was stirred at 70° C. for 1.3 hours. After cooling to room temperature, the reaction mixture was concentrated under a reduced pressure. The residue was diluted with water, neutralized with 1N HCl, extracted twice with CH₂Cl₂, dried over anhydrous MgSO₄, filtered and evaporated under a reduced pressure. The residue was purified by MPLC on NH silica gel eluting with MeOH/CH₂Cl₂ (1%→2%) to obtain the title compound (42.8 mg, 98%) as a pale yellow solid.

MS (ESI) m/z 334.70 (MH⁺).

¹H NMR (300 MHz, CDCl₃) δ 9.00 (s, 1H), 8.17 (d, 1H), 8.10 (d, 1H), 7.60 (dd, 1H), 7.42 (t, 1H), 7.34 (d, 1H), 6.92 (d, 1H), 4.10 (m, 4H), 2.40 (s, 3H).

Example 8: Preparation of 5-benzo[b]thiophen-5-yl-6-(6-methyl-pyridin-2-yl)-2,3-dihydro-1H-imidazo[1,2-a]imidazole

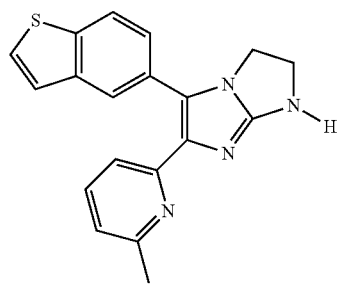 [SMILES: Cc1cccc(-c2nc3n(c2-c2ccc4sccc4c2)CCN3)n1]

Pd(PPh₃)₄ (15 mg, 0.013 mmol) was added to a suspension of 2-benzo[b]thiophen-5-yl-4,4,5,5-tetramethyl-[1,3,2]dioxaborolane (Intermediate 3, 80.2 mg, 0.31 mmol), 1-[5-bromo-6-(6-methyl-pyridin-2-yl)-2,3-dihydro-imidazo[1,2-a]imidazol-1-yl]-ethanone (Intermediate 12, 83 mg, 0.26 mmol), K₂CO₃ (72 mg, 0.52 mmol) in toluene (4.5 mL) and EtOH (0.2 mL), and the mixture was stirred at 100° C. under N₂ for 16 hours. After cooling to room temperature, the mixture was filtered through celite, washed with CH₂Cl₂, and concentrated under a reduced pressure. The residue was purified by MPLC on NH silica gel eluting with CH₂Cl₂/hexane/EtOAC (3/1/0.5→2/1/1) and recrysallization from CH₂Cl₂/hexane to obtain the coupled compound (18.2 mg, 19%) as a white solid. To a suspension of the above compound (18.2 mg, 0.049 mmol) in MeOH (2 mL) was added 1N NaOH (63 µL, 0.063 mmol) and the mixture was stirred at 70° C. for 2 hours. After cooling to room temperature, the reaction mixture was concentrated under a reduced pressure. The residue was diluted with water, neutralized with 1N HCl, extracted twice with CH₂Cl₂, dried over anhydrous MgSO₄, filtered and evaporated under a reduced pressure. The residue was purified by MPLC on NH silica gel eluting with MeOH/CH₂Cl₂ (1%→2%) to obtain the title compound (16.0 mg, 99%) as a pale brown solid.

MS (ESI) m/z 333.71 (MH⁺).

¹H NMR (300 MHz, CDCl₃) δ 7.95 (d, 1H), 7.84 (d, 1H), 7.46 (d, 1H), 7.43 (dd, 1H), 7.38 (d, 1H), 7.32 (t, 1H), 7.26 (d, 1H), 6.90 (d, 1H), 4.35 (br s, 1H), 4.06 (m, 4H), 2.46 (s, 3H).

Example 9: Preparation of 6-[2-(6-methyl-pyridin-2-yl)-6,7-dihydro-5H-imidazo[1,2-a]imidazol-3-yl]-[1,2,4]triazolo[1,5-a]pyridine

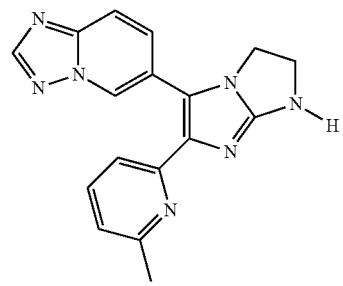 [SMILES: Cc1cccc(-c2nc3n(c2-c2ccc4ncnn4c2)CCN3)n1]

The procedure described for Example 8 was repeated except that 6-(4,4,5,5-tetramethyl-[1,3,2]dioxaborolan-2-yl)-[1,2,4]triazolo[1,5-a]pyridine (Intermediate 4, 100 mg, 0.41 mmol) was used instead of 2-benzo[b]thiophen-5-yl-1-4,4,5,5-tetramethyl-[1,3,2]dioxaborolane, and MPLC on NH silica gel elution was conducted with CH₂Cl₂/EtOAC/hexane (3/1/0.5→3/0/1) to obtain the coupled compound (45.3 mg, 31%) as a white solid. The resulting compound was then reacted as described in Example 8 to afford after MPLC on NH silica gel eluting with MeOH/CH₂Cl₂ (1→2%), the title compound (35.7 mg, 89%) as a pale yellow solid.

MS (ESI) m/z 318.71 (MH⁺).

¹H NMR (300 MHz, CDCl₃) δ 9.01 (t, 1H), 8.31 (s, 1H), 7.66 (m, 1H), 7.56 (d, 1H), 7.52 (t, 1H), 6.94 (dd, 1H), 5.39 (br s, 1H), 4.03 (m, 4H), 2.37 (s, 3H).

Example 10: Preparation of 5-[2-(6-methyl-pyridin-2-yl)-6,7-dihydro-5H-imidazo[1,2-a]imidazol-3-yl]-benzoxazole

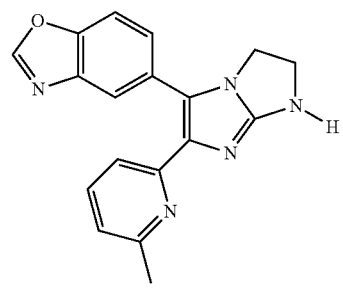 [SMILES: Cc1cccc(-c2nc3n(c2-c2ccc4ocnc4c2)CCN3)n1]

The procedure described for Example 8 was repeated except that 5-(4,4,5,5-tetramethyl-[1,3,2]dioxaborolan-2-yl)-benzoxazole (Intermediate 5, 92.4 mg, 0.38 mmol) was used instead of 2-benzo[b]thiophen-5-yl-4,4,5,5-tetramethyl-[1,3,2]dioxaborolane, and MPLC on NH silica gel elution was conducted with CH₂Cl₂/EtOAC/hexane (3/1/1) and recrystallization from CH₂Cl₂/hexane, to obtain the coupled compound (27.9 mg, 25%) as a white solid. The resulting compound was then reacted as described in Example 8 to afford after MPLC on NH silica gel eluting with MeOH/CH$_2$Cl$_2$ (1→2%), the title compound (7.4 mg, 30%) as a pale yellow solid.

MS (ESI) m/z 318.69 (MH$^+$).

$^1$H NMR (300 MHz, CDCl$_3$) δ 8.12 (s, 1H), 7.90 (s, 1H), 7.55 (d, 2H), 7.41 (t, 1H), 7.30 (d, 1H), 6.90 (d, 1H), 4.07 (m, 4H), 2.42 (s, 3H).

Example 11: Preparation of 4-[2-(6-methyl-pyridin-2-yl)-6,7-dihydro-5H-imidazo[1,2-a]imidazol-3-yl]-quinoline

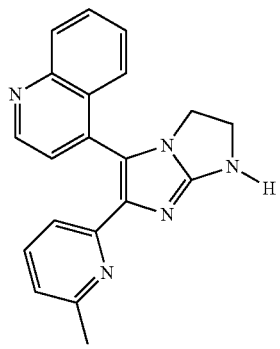 [SMILES: Cc1cccc(-c2nc3n(c2-c2ccnc4ccccc24)CCN3)n1]

The procedure described for Example 8 was repeated except that 4-(4,4,5,5-tetramethyl-[1,3,2]dioxaborolan-2-yl)-quinoline (Intermediate 6, 92.3 mg, 0.36 mmol) was used instead of 2-benzo[b]thiophen-5-yl-4,4,5,5-tetramethyl-[1,3,2]dioxaborolane, and MPLC on NH silica gel elution was conducted with CH$_2$Cl$_2$/EtOAC/hexane (2/0.5/1→2/1/0) to obtain the coupled compound (18.4 mg, 17%) as a pale yellow solid. The resulting compound was then reacted as described in Example 8 to afford after MPLC on NH silica gel eluting with MeOH/CH$_2$Cl$_2$ (1%→2%), the title compound (14.8 mg, 91%) as a yellow solid.

MS (ESI) m/z 328.74 (MH$^+$).

$^1$H NMR (300 MHz, CDCl$_3$) δ 8.94 (d, 1H), 8.14 (d, 1H), 7.82 (d, 1H), 7.69 (m, 1H), 7.45 (d, 1H), 7.39 (m, 1H), 7.33 (t, 1H), 7.22 (d, 1H), 6.79 (d, 1H), 4.57 (br s, 1H), 4.06 (t, 2H), 3.90 (m, 2H), 2.09 (s, 3H).

Example 12: Preparation of 5-benzo[1,3]dioxol-5-yl-6-(6-methyl-pyridin-2-yl)-2,3-dihydro-1H-imidazo[1,2-a]imidazole

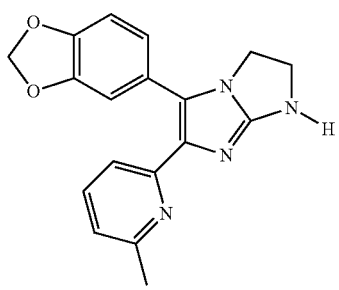 [SMILES: Cc1cccc(-c2nc3n(c2-c2ccc4c(c2)OCO4)CCN3)n1]

The procedure described for Example 8 was repeated except that 5-(4,4,5,5-tetramethyl-[1,3,2]dioxaborolan-2-yl)-benzo[1,3]dioxole (Intermediate 7, 92 mg, 0.37 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/1) and recrystallization from CH$_2$Cl$_2$/hexane, to obtain the coupled compound (34.0 mg, 30%) as a white solid. The resulting compound was then reacted as described in Example 8 to afford after MPLC on NH silica gel eluting with MeOH/CH$_2$Cl$_2$ (1→2%), the title compound (26.5 mg, 88%) as a pale brown solid.

MS (ESI) m/z 321.61 (MH$^+$).

$^1$H NMR (300 MHz, CDCl$_3$) δ 7.40 (t, 1H), 7.26 (d, 1H), 6.98 (d, 1H), 6.91 (m, 2H), 6.80 (d, 1H), 5.98 (s, 2H), 4.35 (br s, 1H), 4.02 (m, 4H), 2.48 (s, 3H).

Example 13: Preparation of 5-(2,3-dihydro-benzo[1,4]dioxin-6-yl)-6-(6-methyl-pyridin-2-yl)-2,3-dihydro-1H-imidazo[1,2-a]imidazole

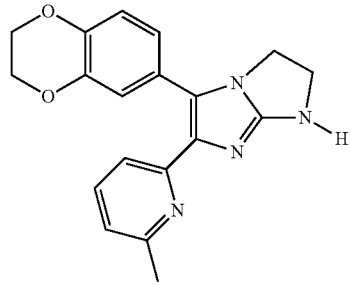 [SMILES: Cc1cccc(-c2nc3n(c2-c2ccc4c(c2)OCCO4)CCN3)n1]

The procedure described for Example 8 was repeated except that 6-(4,4,5,5-tetramethyl-[1,3,2]dioxaborolan-2-yl)-2,3-dihydro-benzo[1,4]dioxine (Intermediate 8, 98 mg, 0.37 mmol) was used instead of 2-benzo[b]thiophen-5-yl)-4,4,5,5-tetramethyl-[1,3,2]dioxaborolane, and MPLC on NH silica gel elution was conducted with CH$_2$Cl$_2$/EtOAC/hexane (3/0.5/1) and recrystallization from CH$_2$Cl$_2$/hexane to obtain the coupled compound (33.3 mg, 29%) as a white solid. The resulting compound was then reacted as described in Example 8 to afford after MPLC on NH silica gel eluting with MeOH/CH$_2$Cl$_2$ (1→2%), the title compound (28.5 mg, 96%) as a pale brown solid.

MS (ESI) m/z 335.69 (MH$^+$).

$^1$H NMR (300 MHz, CDCl$_3$) δ 7.39 (t, 1H), 7.17 (d, 1H), 6.90 (d, 1H), 6.88 (d, 1H), 6.83 (dd, 1H), 6.77 (d, 1H), 4.23 (m, 4H), 3.97 (m, 4H), 2.42 (s, 3H).

Example 14: Preparation of 7-[2-(6-methyl-pyridin-2-yl)-6,7-dihydro-5H-imidazo[1,2-a]imidazol-3-yl]-2-pyrazol-1-yl-quinoxaline

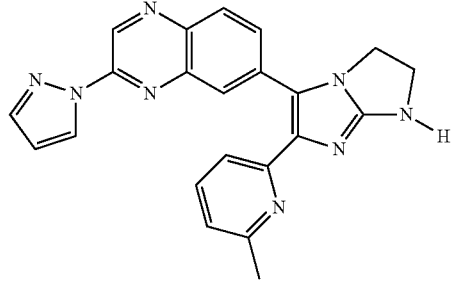 [SMILES: Cc1cccc(-c2nc3n(c2-c2ccc4ncc(-n5cccn5)nc4c2)CCN3)n1]

The procedure described for Example 8 was repeated except that 2-pyrazol-1-yl-7-(4,4,5,5-tetramethyl-[1,3,2]dioxaborolan-2-yl)-quinoxaline (Intermediate 10, 102 mg, 0.35 mmol) was used instead of 2-benzo[b]thiophen-5-yl)-4,4,5,5-tetramethyl-[1,3,2]dioxaborolane, and MPLC on NH silica gel elution was conducted with CH$_2$Cl$_2$/EtOAC/hexane (2/0.5/1) and recrystallization from CH$_2$Cl$_2$/hexane to obtain the coupled compound (52.6 mg, 39%) as a white solid. The resulting compound was then reacted as described in Example 8 to afford after MPLC on NH silica gel eluting with MeOH/CH$_2$Cl$_2$ (1→2%) and recrystallization three times from CH$_2$Cl$_2$/hexane, the title compound (25.4 mg, 53%) as an orange solid.

MS (ESI) m/z 395.78 (MH$^+$).

$^1$H NMR (300 MHz, CDCl$_3$+CD$_3$OD) δ 9.56 (s, 1H), 8.67 (d, 1H), 8.02 (d, 1H), 7.96 (d, 1H), 7.84 (m, 1H), 7.77 (dd, 1H), 7.51 (t, 1H), 7.41 (d, 1H), 6.97 (d, 1H), 6.56 (m, 1H), 4.23 (m, 2H), 4.06 (m, 2H), 2.36 (s, 3H).

Example 15: Preparation of dimethyl-(2-{7-[2-(6-methyl-pyridin-2-yl)-6,7-dihydro-5H-imidazo[1,2-a]imidazol-3-yl]-quinoxalin-2-yloxy}-ethyl)-amine

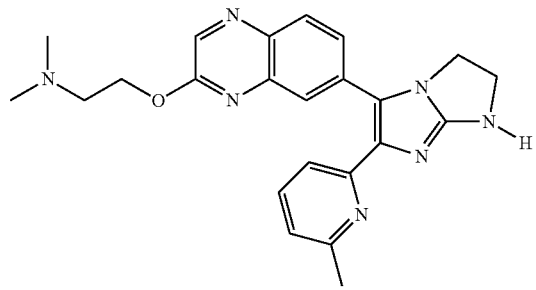 [SMILES: Cc1cccc(-c2nc3n(c2-c2ccc4ncc(OCCN(C)C)nc4c2)CCN3)n1]

2-Dimethylaminoethanol (0.6 mL) was added to a suspension of 1-[6-(6-methyl-pyridin-2-yl)-5-(3-pyrazol-1-yl-quinoxalin-6-yl)-2,3-dihydro-imidazo[1,2-a]imidazol-1-yl]-ethanone (see the procedure described for Example 14, 25.5 mg, 0.058 mmol) and K$_2$CO$_3$ (24.2 mg, 0.175 mmol) in DMF (0.8 mL), and the mixture was stirred at 120° C. for 4 hours. After cooling to room temperature, the mixture was concentrated under a reduced pressure. The residue was diluted with water, neutralized with 1N HCl, extracted three times with CH$_2$Cl$_2$, dried over anhydrous MgSO$_4$, filtered and evaporated under a reduced pressure. The residue was purified by MPLC on NH silica gel eluting with MeOH/CH$_2$Cl$_2$ (1→2%) to obtain the title compound (10.5 mg, 43%) as a yellow solid.

MS (ESI) m/z 416.57 (MH$^+$).

$^1$H NMR (300 MHz, CDCl$_3$) δ 8.48 (s, 1H), 7.91 (s, 1H), 7.89 (d, 1H), 7.68 (dd, 1H), 7.46 (t, 1H), 7.40 (d, 1H), 6.95 (d, 1H), 4.89 (br s, 1H), 4.58 (t, 2H), 4.22 (m, 2H), 4.09 (m, 2H), 2.79 (t, 2H), 2.42 (s, 3H), 2.37 (s, 6H).

Example 16: Preparation of 2-methoxy-7-[2-(6-methyl-pyridin-2-yl)-6,7-dihydro-5H-imidazo[1,2-a]imidazol-3-yl]-quinoxaline

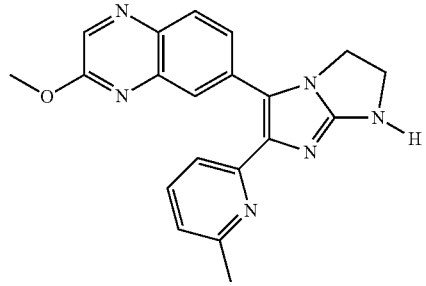 [SMILES: COc1cnc2ccc(-c3c(-c4cccc(C)n4)nc4n3CCN4)cc2n1]

1N NaOH (37 μL, 0.037 mmol) was added to a suspension of 1-[5-(3-imidazol-1-yl-quinoxalin-6-yl)-6-(6-methyl-pyridin-2-yl)-2,3-dihydro-imidazo[1,2-a]imidazol-1-yl]-ethanone (prepared from Intermediate 9 as described in Example 8, 12.3 mg, 0.028 mmol) in MeOH (2 mL), and the mixture was stirred at 70° C. for 1 hour. After cooling to room temperature, the mixture was concentrated under a reduced pressure. The residue was diluted with water, neutralized with 1N HCl, extracted three times with CH$_2$Cl$_2$, dried over anhydrous MgSO$_4$, filtered and evaporated under a reduced pressure. The residue was purified by MPLC on NH silica gel eluting with MeOH/CH$_2$Cl$_2$ (1→2%) to obtain the title compound (9.4 mg, 94%) as a yellow solid.

MS (ESI) m/z 359.74.

$^1$H NMR (400 MHz, CDCl$_3$) δ 8.42 (s, 1H), 7.93 (d, 1H), 7.90 (d, 1H), 7.68 (dd, 1H), 7.46 (t, 1H), 7.40 (d, 1H), 6.95 (d, 1H), 4.46 (br s, 1H), 4.22 (m, 2H), 4.09 (s, 3H), 4.07 (m, 2H), 2.43 (s, 3H).

Example 17: Preparation of 5-(3,5-dimethoxyphenyl)-6-(6-methylpyridin-2-yl)-2,3-dihydro-1H-imidazo[1,2-a]imidazole

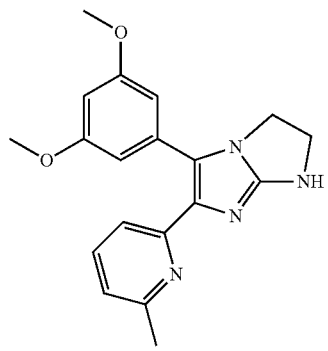 [SMILES: COc1cc(OC)cc(-c2c(-c3cccc(C)n3)nc3n2CCN3)c1]

The procedure described for Example 8 was repeated except that 2-(3,5-dimethoxyphenyl)-4,4,5,5-tetramethyl-1,3,2-dioxaborolane (79 mg, 0.3 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/4) to obtain the coupled compound (30 mg, 40%) as a white solid. The resulting compound was then reacted as described in Example 8 to afford after MPLC on NH silica gel eluting with MeOH/CH$_2$Cl$_2$ (1→3%), the title compound (6.9 mg, 26%) as an off-white solid.

MS (ESI) m/z 337.27 (MH+)
<sup>1</sup>H NMR (300 MHz, CDCl<sub>3</sub>) δ 7.41 (t, 1H), 7.29 (d, 1H), 6.92 (d, 1H), 6.61 (d, 2H), 6.41 (t, 1H), 4.09 (dd, 2H), 4.00 (dd, 2H), 3.74 (s, 6H), 2.51 (s, 3H).

Example 18: Preparation of N,N-dimethyl-4-(6-(6-methylpyridin-2-yl)-2,3-dihydro-1H-imidazo[1,2-a]imidazol-5-yl)aniline

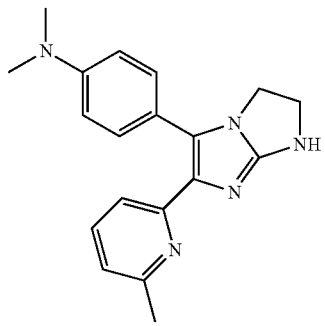 [SMILES: Cc1cccc(-c2nc3n(c2-c2ccc(N(C)C)cc2)CCN3)n1]

The procedure described for Example 8 was repeated except that (4-(dimethylamino)phenyl)boronic acid (50 mg, 0.3 mmol) was used instead of 2-benzo[b]thiophen-5-yl-4,4,5,5-tetramethyl-[1,3,2]dioxaborolane, and MPLC on NH silica gel elution was conducted with CH<sub>2</sub>Cl<sub>2</sub>/EtOAC/hexane (2/0.5/4) to obtain the coupled compound (20 mg, 28%) as a white solid. The resulting compound was then reacted as described in Example 8 to afford after MPLC on NH silica gel eluting with MeOH/CH<sub>2</sub>Cl<sub>2</sub> (1→3%), the title compound (10.4 mg, 58%) as an off-white solid.
MS (ESI) m/z 320.34 (MH+)
<sup>1</sup>H NMR (300 MHz, CDCl<sub>3</sub>) δ 7.33 (m, 3H), 7.21 (m, 1H), 6.88 (m, 1H), 6.71 (m, 2H), 4.00 (ddt, 4H), 2.98 (s, 6H), 2.49 (s, 3H).

Example 19: Preparation of 4-(6-(6-methylpyridin-2-yl)-2,3-dihydro-1H-imidazo[1,2-a]imidazol-5-yl)benzonitrile

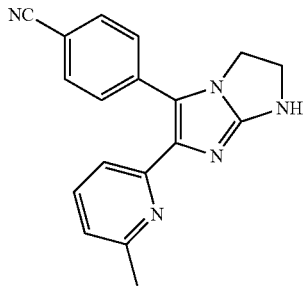 [SMILES: Cc1cccc(-c2nc3n(c2-c2ccc(C#N)cc2)CCN3)n1]

The procedure described for Example 8 was repeated except that 4-(4,4,5,5-tetramethyl-1,3,2-dioxaborolan-2-yl)benzonitrile (103 mg, 0.45 mmol) was used instead of 2-benzo[b]thiophen-5-yl-4,4,5,5-tetramethyl-[1,3,2]dioxaborolane and MPLC on NH silica gel elution was conducted with CH<sub>2</sub>Cl<sub>2</sub>/EtOAC/hexane (2/0.5/4) to obtain the coupled compound (21 mg, 20%) as a yellow solid. The resulting compound was then reacted as described in Example 8 to afford after MPLC on NH silica gel eluting with MeOH/CH<sub>2</sub>Cl<sub>2</sub> (1→3%), the title compound (11.1 mg, 61%) as a pale yellow solid.
MS (ESI) m/z 302.31 (MH+)
<sup>1</sup>H NMR (300 MHz, CDCl<sub>3</sub>) δ 7.57 (m, 5H), 7.39 (d, 1H), 7.01 (d, 1H), 4.09 (m, 4H), 2.40 (s, 3H).

Example 20: Preparation of 2-methyl-6-(6-(6-methylpyridin-2-yl)-2,3-dihydro-1H-imidazo[1,2-a]imidazol-5-yl)quinoline

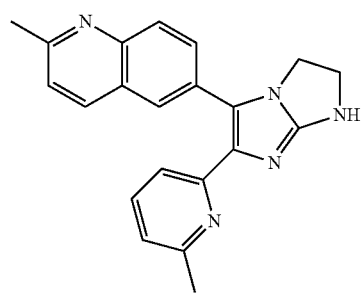 [SMILES: Cc1cccc(-c2nc3n(c2-c2ccc4nc(C)ccc4c2)CCN3)n1]

The procedure described for Example 8 was repeated except that 2-methyl-6-(4,4,5,5-tetramethyl-1,3,2-dioxaborolan-2-yl)quinoline (121 mg, 0.45 mmol) was used instead of 2-benzo[b]thiophen-5-yl-4,4,5,5-tetramethyl-[1,3,2]dioxaborolane and MPLC on NH silica gel elution was conducted with CH<sub>2</sub>Cl<sub>2</sub>/EtOAC/hexane (2/0.5/4) to obtain the coupled compound (47 mg, 41%) as a yellow solid. The resulting compound was then reacted as described in Example 8 to afford after MPLC on NH silica gel eluting with MeOH/CH<sub>2</sub>Cl<sub>2</sub> (1→3%), the title compound (20.4 mg, 49%) as a yellow solid.
MS (ESI) m/z 342.35 (MH+)
<sup>1</sup>H NMR (300 MHz, CDCl<sub>3</sub>) δ 7.94 (m, 3H), 7.77 (dd, 1H), 7.43 (m, 2H), 7.28 (d, 1H), 6.93 (d, 1H), 4.10 (m, 4H), 2.75 (s, 3H), 2.38 (s, 3H).

Example 21: Preparation of 4-(6-(6-methylpyridin-2-yl)-2,3-dihydro-1H-imidazo[1,2-a]imidazol-5-yl)aniline

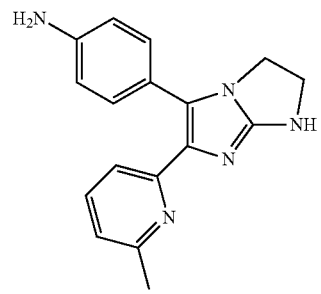 [SMILES: Cc1cccc(-c2nc3n(c2-c2ccc(N)cc2)CCN3)n1]

The procedure described for Example 8 was repeated except that 4-(4,4,5,5-tetramethyl-1,3,2-dioxaborolan-2-yl)aniline (66 mg, 0.3 mmol) was used instead of 2-benzo[13]thiophen-5-yl-4,4,5,5-tetramethyl-[1,3,2]dioxaborolane and MPLC on NH silica gel elution was conducted with CH<sub>2</sub>Cl<sub>2</sub>/EtOAC/hexane (2/0.5/4) to obtain the coupled compound (33 mg, 49%) as a brown solid. The resulting compound was then reacted as described in Example 8 to afford after MPLC on NH silica gel eluting with MeOH/CH$_2$Cl$_2$ (1→3%), the title compound (18.0 mg, 63%) as a pale brown solid.

MS (ESI) m/z 292.30 (MH+)

$^1$H NMR (300 MHz, CDCl$_3$) δ 7.41 (t, 1H), 7.19 (m, 3H), 6.91 (d, 1H), 6.68 (m, 2H), 4.00 (m, 4H), 3.29 (br s, 2H, NH$_2$), 2.46 (s, 3H).

Example 22: Preparation of N-(4-(6-(6-methylpyridin-2-yl)-2,3-dihydro-1H-imidazo[1,2-a]imidazol-5-yl)phenyl)acetamide

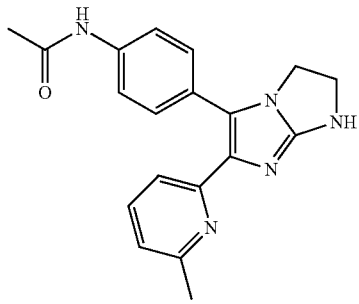 [SMILES: CC(=O)Nc1ccc(-c2c(-c3cccc(C)n3)nc3n2CCN3)cc1]

The procedure described for Example 8 was repeated except that N-(4-(4,4,5,5-tetramethyl-1,3,2-dioxaborolan-2-yl)phenyl)acetamide (79 mg, 0.3 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/4) to obtain the coupled compound (23 mg, 31%) as a yellow solid. The resulting compound was then reacted as described in Example 8 to afford after MPLC on NH silica gel eluting with MeOH/CH$_2$Cl$_2$ (1→3%), the title compound (2.2 mg, 11%) as a pale yellow solid.

MS (ESI) m/z 334.30 (MH+)

$^1$H NMR (300 MHz, CDCl$_3$) δ 7.44 (m, 5H), 7.27 (d, 1H), 6.92 (d, 1H), 4.02 (m, 4H), 2.44 (s, 3H), 2.17 (s, 3H).

Example 23: Preparation of N-(4-(6-(6-methylpyridin-2-yl)-2,3-dihydro-1H-imidazo[1,2-a]imidazol-5-yl)phenyl)methanesulfonamide

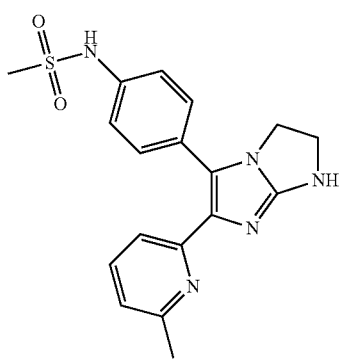 [SMILES: Cc1cccc(-c2nc3n(c2-c2ccc(NS(C)(=O)=O)cc2)CCN3)n1]

The procedure described for Example 8 was repeated except that 4-(4,4,5,5-tetramethyl-1,3,2-dioxaborolan-2-yl)aniline (132 mg, 0.6 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/4) to obtain the coupled compound (66 mg, 49%) as a brown solid.

Methanesulfonyl chloride (33 µL, 0.4 mmol) was added to a solution of the coupled compound (66 mg, 0.2 mmol) and triethylamine (111 µL, 0.8 mmol) in dry CH$_2$Cl$_2$ (2 mL), and the mixture was stirred at 40° C. under N$_2$ for 1 hour. After cooling to room temperature, the mixture was diluted with brine and CH$_2$Cl$_2$, and stirred for 5 minutes. After separating organic layer, the aqueous layer was extracted three times with CH$_2$Cl$_2$, dried over Na$_2$SO$_4$, filtered, and concentrated under a reduced pressure. The residue was purified by MPLC on NH silica gel eluting solvent (CH$_2$Cl$_2$/hexane/EtOAC (3/1/1)→MeOH/CH$_2$Cl$_2$ (1/20)). The resulting compound was then reacted with 1N NaOH as described in Example 8 to afford after MPLC on NH silica gel eluting with MeOH/CH$_2$Cl$_2$ (3→10%), the title compound (34.7 mg, 47% in two steps) as a pale brown solid.

MS (ESI) m/z 370.07 (MH+)

$^1$H NMR (300 MHz, CDCl$_3$) δ 7.42 (t, 1H), 7.30 (m, 2H), 7.21 (d, 1H), 7.14 (m, 2H), 6.89 (d, 1H), 3.98 (m, 4H), 2.94 (s, 3H), 2.34 (s, 3H).

Example 24: Preparation of tert-butyl (4-(6-(6-methylpyridin-2-yl)-2,3-dihydro-1H-imidazo[1,2-a]imidazol-5-yl)phenyl)carbamate

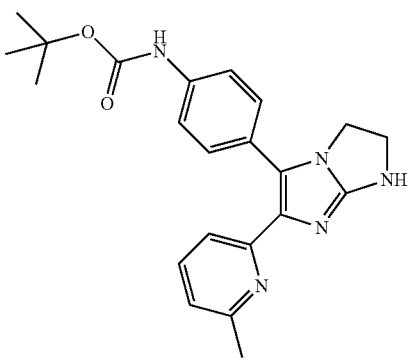 [SMILES: Cc1cccc(-c2nc3n(c2-c2ccc(NC(=O)OC(C)(C)C)cc2)CCN3)n1]

The procedure described for Example 8 was repeated except that tert-butyl (4-(4,4,5,5-tetramethyl-1,3,2-dioxaborolan-2-yl)phenyl) carbamate (144 mg, 0.45 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/4) to obtain the coupled compound (33 mg, 25%) as a white solid. The resulting compound was then reacted as described in Example 8 to afford after MPLC on NH silica gel eluting with MeOH/CH$_2$Cl$_2$ (1→3%), the title compound (12.4 mg, 42%) as an off-white solid.

MS (ESI) m/z 392.16 (MH+)

$^1$H NMR (300 MHz, CDCl$_3$) δ 7.42 (t, 2H), 7.35 (m, 4H), 7.24 (d, 1H), 6.92 (d, 1H), 4.01 (m, 4H), 2.45 (s, 3H), 1.53 (s, 9H).

Example 25: Preparation of 5-(4-(4-methylpiperazin-1-yl)phenyl)-6-(6-methylpyridin-2-yl)-2,3-dihydro-1H-imidazo[1,2-a]imidazole

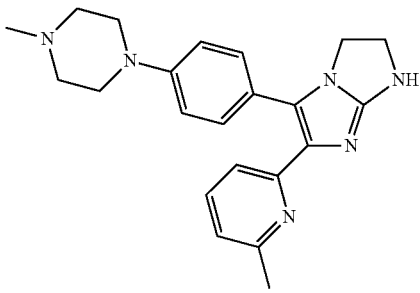 [SMILES: Cc1cccc(-c2nc3n(c2-c2ccc(N4CCN(C)CC4)cc2)CCN3)n1]

The procedure described for Example 8 was repeated except that 1-methyl-4-(4-(4,4,5,5-tetramethyl-1,3,2-dioxaborolan-2-yl)phenyl)piperazine (136 mg, 0.45 mmol) was used instead of 2-benzo[b]thiophen-5-yl-4,4,5,5-tetramethyl-[1,3,2]dioxaborolane and MPLC on NH silica gel elution was conducted with $CH_2Cl_2$/EtOAC/hexane (2/0.5/4) to obtain the coupled compound (58 mg, 46%) as a white solid. The resulting compound was then reacted as described in Example 8 to afford after MPLC on NH silica gel eluting with MeOH/$CH_2Cl_2$ (1→3%), the title compound (53.9 mg, 99%) as an off-white solid.

MS (ESI) m/z 375.37 (MH+)

$^1$H NMR (300 MHz, CDCl$_3$) δ 7.40 (t, 1H), 7.32 (m, 2H), 7.22 (d, 1H), 6.90 (m, 3H), 3.99 (m, 4H), 3.25 (dd, 4H), 2.60 (dd, 4H), 2.47 (s, 3H), 2.36 (s, 3H).

Example 26: Preparation of 4-(4-(6-(6-methylpyridin-2-yl)-2,3-dihydro-1H-imidazo[1,2-a]imidazol-5-yl)phenyl)morpholine

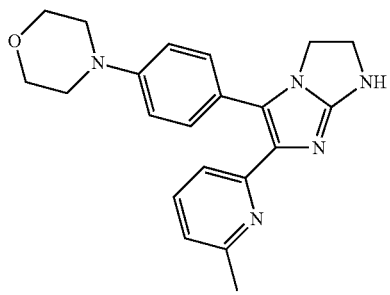 [SMILES: Cc1cccc(-c2nc3n(c2-c2ccc(N4CCOCC4)cc2)CCN3)n1]

The procedure described for Example 8 was repeated except that 4-(4-(4,4,5,5-tetramethyl-1,3,2-dioxaborolan-2-yl)phenyl)morpholine (131 mg, 0.45 mmol) was used instead of 2-benzo[b]thiophen-5-yl-4,4,5,5-tetramethyl-[1,3,2]dioxaborolane and MPLC on NH silica gel elution was conducted with $CH_2Cl_2$/EtOAC/hexane (2/0.5/4) to obtain the coupled compound (66 mg, 55%) as a white solid. The resulting compound was then reacted as described in Example 8 to afford after MPLC on NH silica gel eluting with MeOH/$CH_2Cl_2$ (1→3%), the title compound (34.5 mg, 58%) as an off-white solid.

MS (ESI) m/z 362.42 (MH+)

$^1$H NMR (300 MHz, CDCl$_3$) δ 7.41 (t, 1H), 7.33 (m, 2H), 7.22 (d, 1H), 6.89 (m, 3H), 4.01 (m, 4H), 3.88 (dd, 4H), 3.20 (dd, 4H), 2.47 (s, 3H).

Example 27: Preparation of 6-(6-methylpyridin-2-yl)-5-(m-tolyl)-2,3-dihydro-1H-imidazo[1,2-a]imidazole

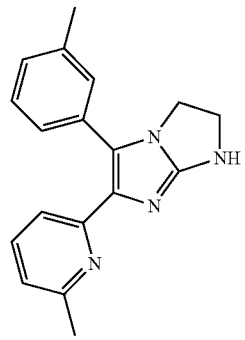 [SMILES: Cc1cccc(-c2c(-c3cccc(C)n3)nc3n2CCN3)c1]

The procedure described for Example 8 was repeated except that m-tolylboronic acid (62 mg, 0.45 mmol) was used instead of 2-benzo[b]thiophen-5-yl)-4,4,5,5-tetramethyl-[1,3,2]dioxaborolane and MPLC on NH silica gel elution was conducted with $CH_2Cl_2$/EtOAC/hexane (2/0.5/4) to obtain the coupled compound (34 mg, 34%) as a white solid. The resulting compound was then reacted as described in Example 8 to afford after MPLC on NH silica gel eluting with MeOH/$CH_2Cl_2$ (1→3%), the title compound (31.3 mg, 99%) as an off-white solid.

MS (ESI) m/z 291.32 (MH+)

$^1$H NMR (300 MHz, CDCl$_3$) δ 7.41 (t, 1H), 7.26 (m, 4H), 7.10 (m, 1H), 6.91 (d, 1H), 4.03 (m, 4H), 2.46 (s, 3H), 2.34 (t, 3H).

Example 28: Preparation of 5-(4-methoxyphenyl)-6-(6-methylpyridin-2-yl)-2,3-dihydro-1H-imidazo[1,2-a]imidazole

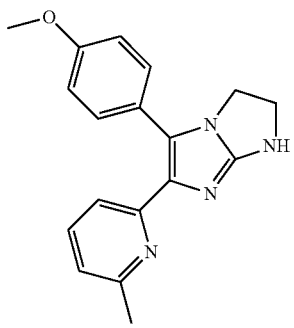

The procedure described for Example 8 was repeated except that (4-methoxyphenyl)boronic acid (69 mg, 0.45 mmol) was used instead of 2-benzo[b]thiophen-5-yl-4,4,5,5-tetramethyl-[1,3,2]dioxaborolane and MPLC on NH silica gel elution was conducted with $CH_2Cl_2$/EtOAC/hexane (2/0.5/4) to obtain the coupled compound (42 mg, 40%) as a white solid. The resulting compound was then reacted as described in Example 8 to afford after MPLC on NH silica gel eluting with MeOH/CH$_2$Cl$_2$ (1→3%), the title compound (22.1 mg, 60%) as an off-white solid.

MS (ESI) m/z 307.30 (MH+)

$^1$H NMR (300 MHz, CDCl$_3$) δ 7.39 (m, 3H), 7.26 (m, 1H), 6.90 (m, 3H), 4.02 (m, 4H), 3.84 (s, 3H), 2.46 (s, 3H).

Example 29: Preparation of 6-(6-methylpyridin-2-yl)-5-(4-(trifluoromethyl) phenyl)-2,3-dihydro-1H-imidazo[1,2-a]imidazole

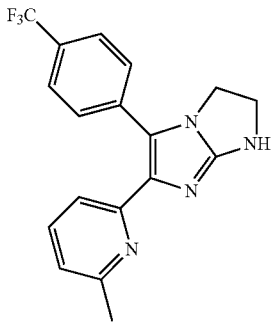 [SMILES: Cc1cccc(-c2nc3n(c2-c2ccc(C(F)(F)F)cc2)CCN3)n1]

The procedure described for Example 8 was repeated except that (4-(trifluoromethyl)phenyl)boronic acid (86 mg, 0.45 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/4) to obtain the coupled compound (48 mg, 41%) as a white solid. The resulting compound was then reacted as described in Example 8 to afford after MPLC on NH silica gel eluting with MeOH/CH$_2$Cl$_2$ (1→3%), the title compound (22.0 mg, 52%) as an off-white solid.

MS (ESI) m/z 345.37 (MH+)

$^1$H NMR (300 MHz, CDCl$_3$) δ 7.59 (m, 4H), 7.49 (t, 1H), 7.38 (d, 1H), 6.96 (d, 1H), 4.06 (m, 4H), 2.42 (s, 3H).

Example 30: Preparation of 6-(6-methylpyridin-2-yl)-5-(4-(methylthio) phenyl)-2,3-dihydro-1H-imidazo[1,2-a]imidazole

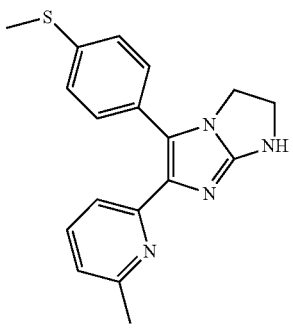 [SMILES: CSc1ccc(-c2c(-c3cccc(C)n3)nc3n2CCN3)cc1]

The procedure described for Example 8 was repeated except that (4-(methylthio)phenyl)boronic acid (76 mg, 0.45 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/4) to obtain the coupled compound (19 mg, 17%) as a white solid. The resulting compound was then reacted as described in Example 8 to afford after MPLC on NH silica gel eluting with MeOH/CH$_2$Cl$_2$ (1→3%), the title compound (6.1 mg, 37%) as an off-white solid.

MS (ESI) m/z 323.29 (MH+)

$^1$H NMR (300 MHz, CDCl$_3$) δ 7.41 (m, 3H), 7.27 (m, 3H), 6.92 (d, 1H), 4.03 (m, 4H), 2.51 (s, 3H), 2.46 (s, 3H).

Example 31: Preparation of 5-(3-fluoro-4-methoxyphenyl)-6-(6-methylpyridin-2-yl)-2,3-dihydro-1H-imidazo[1,2-a]imidazole

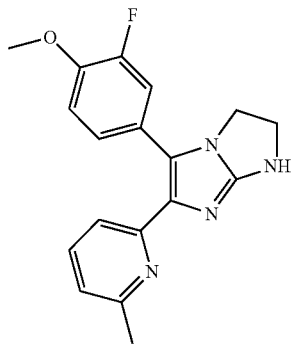 [SMILES: COc1ccc(-c2c(-c3cccc(C)n3)nc3n2CCN3)cc1F]

The procedure described for Example 8 was repeated except that (3-fluoro-4-methoxyphenyl)boronic acid (77 mg, 0.45 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/4) to obtain the coupled compound (26 mg, 24%) as a white solid. The resulting compound was then reacted as described in Example 8 to afford after MPLC on NH silica gel eluting with MeOH/CH$_2$Cl$_2$ (1→3%), the title compound (21.0 mg, 90%) as an off-white solid.

MS (ESI) m/z 325.36 (MH+)

$^1$H NMR (300 MHz, CDCl$_3$) δ 7.45 (t, 1H), 7.31 (m, 2H), 7.17 (ddd, 1H), 6.93 (m, 2H), 4.03 (m, 4H), 3.92 (s, 3H), 2.45 (s, 3H).

Example 32: Preparation of 5-(4-fluorophenyl)-6-(6-methylpyridin-2-yl)-2,3-dihydro-1H-imidazo[1,2-a]imidazole

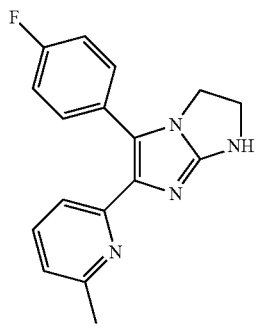 [SMILES: Cc1cccc(-c2nc3n(c2-c2ccc(F)cc2)CCN3)n1]

The procedure described for Example 8 was repeated except that (4-fluorophenyl)boronic acid (64 mg, 0.6 mmol) was used instead of 2-benzo[b]thiophen-5-yl-4,4,5,5-tetramethyl-[1,3,2]dioxaborolane and MPLC on NH silica gel elution was conducted with CH$_2$Cl$_2$/EtOAC/hexane (2/0.5/4) to obtain the coupled compound (40 mg, 40%) as a white solid. The resulting compound was then reacted as described in Example 8 to afford after MPLC on NH silica gel eluting with MeOH/CH$_2$Cl$_2$ (1→3%), the title compound (25.6 mg, 72%) as an off-white solid.

MS (ESI) m/z 295.38 (MH+)

$^1$H NMR (300 MHz, CDCl$_3$) δ 7.45 (m, 3H), 7.31 (d, 1H), 7.04 (m, 2H), 6.90 (d, 1H), 4.03 (m, 4H), 2.43 (s, 3H).

Example 33: Preparation of 1-acetyl-6-(6-methyl-pyridin-2-yl)-5-thieno[3,2-c]pyridin-2-yl-2,3-dihydro-1H-imidazo[1,2-a]imidazole-2-carboxylic acid ethyl ester

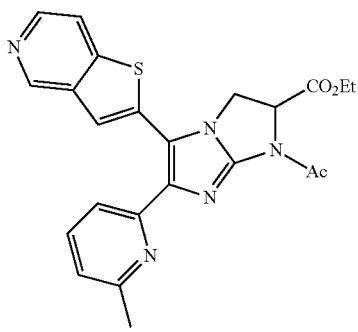 [SMILES: CCOC(=O)C1Cn2c(nc(-c3cccc(C)n3)c2-c2cc3cnccc3s2)N1C(C)=O]

The procedure described for Example 6 was repeated except that 1-acetyl-5-bromo-6-(6-methyl-pyridin-2-yl)-2,3-dihydro-1H-imidazo[1,2-a]imidazole-2-carboxylic acid ethyl ester (Intermediate 16, 414.7 mg, 1.05 mmol) was used instead of 1-[5-bromo-6-(6-methyl-pyridin-2-yl)-2,3-dihydro-imidazo[1,2-a]imidazol-1-yl]-ethanone and MPLC on NH silica gel elution was conducted with CH$_2$Cl$_2$/hexane/EtOAC (3/1/0→3/1/1), to obtain the title compound (298.4 mg, 64%) as an off-white solid.

MS (ESI) m/z 448.31 (MH+)

$^1$H NMR (300 MHz, CDCl$_3$) δ 9.05 (s, 1H), 8.43 (d, 1H), 7.80 (s, 1H), 7.72 (d, 1H), 7.67 (d, 1H), 7.61 (t, 1H), 7.07 (d, 1H), 5.44 (dd, 1H), 4.59 (t, 1H), 4.33 (dd, 1H), 4.29 (q, 2H), 2.76 (s, 3H), 2.56 (s, 3H), 1.32 (t, 3H).

Example 34: Preparation of 6-(6-methyl-pyridin-2-yl)-5-thieno[3,2-c]pyridin-2-yl-2,3-dihydro-1H-imidazo[1,2-a]imidazole-2-carboxylic acid ethyl ester

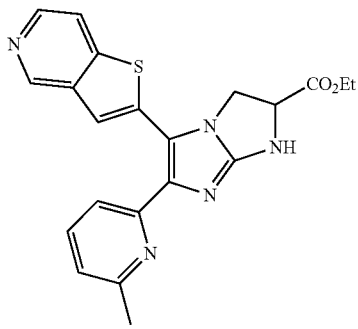 [SMILES: CCOC(=O)C1Cn2c(nc(-c3cccc(C)n3)c2-c2cc3cnccc3s2)N1]

K$_2$CO$_3$ (152 mg, 1.1 mmol) was added to a solution of 1-acetyl-6-(6-methyl-pyridin-2-yl)-5-thieno[3,2-c]pyridin-2-yl-2,3-dihydro-1H-imidazo[1,2-a]imidazole-2-carboxylic acid ethyl ester (Example 33, 50 mg, 0.11 mmol) in EtOH/CH$_2$Cl$_2$ (1/1, 2 mL), and the mixture was stirred for 2 hours and then at 50° C. for 2.5 hours. After cooling to room temperature, the mixture was filtered through celite, washed with 5% MeOH/CH$_2$Cl$_2$ and concentrated under a reduced pressure. The residue was purified by MPLC on NH silica gel eluting with CH$_2$Cl$_2$ to obtain the title compound (4.5 mg, 10%) as a pale brown solid.

MS (ESI) m/z 406.19 (MH+)

$^1$H NMR (300 MHz, CDCl$_3$) δ 9.02 (d, 1H), 8.40 (d, 1H), 7.74 (s, 1H), 7.70 (d, 2H), 7.58 (s, 1H), 7.56 (d, 1H), 7.03 (t, 1H), 4.94 (br s, 1H), 4.83 (dd, 1H), 4.57 (t, 1H), 4.54 (d, 1H), 4.30 (q, 2H), 2.58 (s, 3H), 1.34 (t, 3H).

Example 35: Preparation of [6-(6-methyl-pyridin-2-yl)-5-thieno[3,2-c]pyridin-2-yl-2,3-dihydro-1H-imidazo[1,2-a]imidazol-2-yl]-methanol

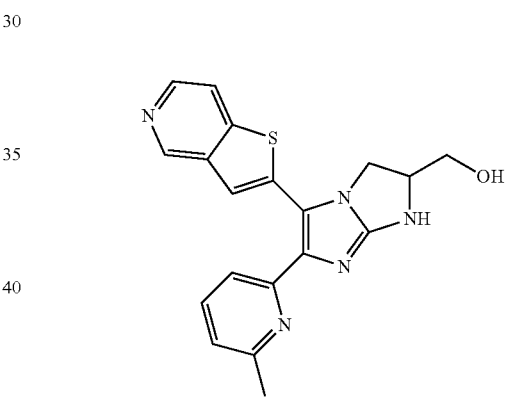

NaBH$_4$ (32 mg, 0.88 mmol) was added to a solution of 1-acetyl-6-(6-methyl-pyridin-2-yl)-5-thieno[3,2-c]pyridin-2-yl-2,3-dihydro-1H-imidazo[1,2-a]imidazole-2-carboxylic acid ethyl ester (Example 33, 50 mg, 0.11 mmol) in EtOH (2 mL) and CH$_2$Cl$_2$ (0.5 ml) at 0° C., and the mixture was stirred for 1 hour. The reaction mixture was quenched with H$_2$O (1 mL) and then added sat. aqueous NH$_4$Cl solution. The mixture was extracted three times with CH$_2$Cl$_2$. The organic layers were combined, dried over Na$_2$SO$_4$, filtered, and concentrated under a reduced pressure. The residue was purified by recrystallization from CH$_2$Cl$_2$/MeOH/Hexane to afford the title compound (31.7 mg, 79%) as a yellow solid.

MS (ESI) m/z 364.32 (MH+)

$^1$H NMR (300 MHz, CDCl$_3$) δ 8.83 (s, 1H), 8.22 (d, 1H), 7.64 (d, 1H), 7.55 (s, 1H), 7.53 (t, 1H), 7.36 (d, 1H), 7.00 (d, 1H), 4.40 (m, 1H), 4.30 (t, 1H), 4.03 (dd, 1H), 4.68 (dd, 1H), 3.61 (dd, 1H), 2.50 (s, 3H).

Example 36: Preparation of 1-acetyl-6-(6-methyl-pyridin-2-yl)-5-thieno[3,2-c]pyridin-2-yl-2,3-dihydro-1H-imidazo[1,2-a]imidazole-2-carbonitrile

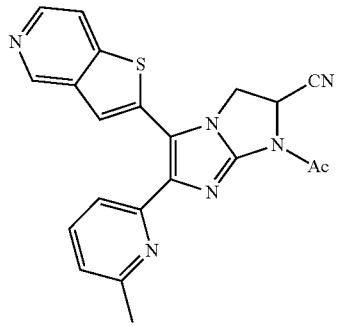 [SMILES: CC(=O)N1c2nc(-c3cccc(C)n3)c(-c3cc4cnccc4s3)n2CC1C#N]

The procedure described for Example 6 was repeated except that 1-acetyl-5-bromo-6-(6-methyl-pyridin-2-yl)-2,3-dihydro-1H-imidazo[1,2-a]imidazole-2-carboxylic acid ethyl ester (Intermediate 18, 240 mg, 0.69 mmol) was used instead of 1-[5-bromo-6-(6-methyl-pyridin-2-yl)-2,3-dihydro-imidazo[1,2-a]imidazol-1-yl]-ethanone. The crude product was purified by MPLC on NH silica gel eluting with $CH_2Cl_2$/hexane/EtOAC (3/1/1) and then recrystallization from $CH_2Cl_2$/MeOH/Hexane to afford the title compound (168.3 mg, 61%) as a pale brown solid.

MS (ESI) m/z 401.19 (MH+)

$^1$H NMR (300 MHz, CDCl$_3$) δ 8.97 (s, 1H), 8.34 (d, 1H), 7.73 (d, 1H), 7.72 (s, 1H), 7.59 (m, 2H), 7.07 (m, 1H), 5.69 (dd, 1H), 4.61 (m, 2H), 2.71 (s, 3H), 2.50 (s, 3H).

Example 37: Preparation of 6-(6-methyl-pyridin-2-yl)-5-thieno[3,2-c]pyridin-2-yl-2,3-dihydro-1H-imidazo[1,2-a]imidazole-2-carbonitrile

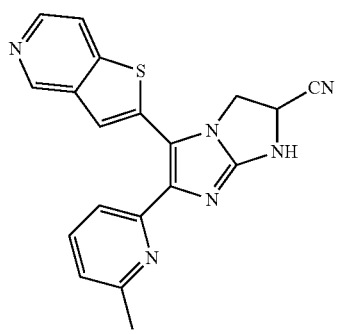 [SMILES: Cc1cccc(-c2nc3n(c2-c2cc4cnccc4s2)CC(C#N)N3)n1]

1N NaOH (80 µL, 0.08 mmol) was added to a solution of 1-acetyl-6-(6-methyl-pyridin-2-yl)-5-thieno[3,2-c]pyridin-2-yl-2,3-dihydro-1H-imidazo[1,2-a]imidazole-2-carbonitrile (Example 36, 50 mg, 0.13 mmol) in MeOH (1 mL) and 1,4-dioxane (4 ml), and the mixture was stirred for 1 hour. The reaction mixture was quenched with sat. aqueous NH$_4$Cl solution and then added H$_2$O. The mixture was extracted three times with CH$_2$Cl$_2$. The organic layers were combined, dried over Na$_2$SO$_4$, filtered, and concentrated under a reduced pressure. The residue was purified by MPLC on NH silica gel eluting with MeOH/CH$_2$Cl$_2$ (0%→2%) to afford the title compound (5.4 mg, 12%) as an off-white solid.

MS (ESI) m/z 359.23 (MH+)

$^1$H NMR (300 MHz, CDCl$_3$) δ 8.86 (s, 1H), 8.24 (d, 1H), 7.66 (d, 1H), 7.56 (s, 1H), 7.51 (d, 1H), 7.36 (d, 1H), 7.02 (d, 1H), 5.10 (dd, 1H), 4.49 (m, 2H), 2.47 (s, 3H).

Example 38: Preparation of 6-(6-methyl-pyridin-2-yl-5-thieno[3,2-c]pyridin-2-yl-2,3-dihydro-1H-imidazo[1,2-a]imidazole-2-carboxylic acid amide

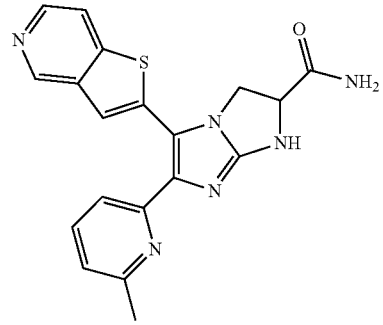 [SMILES: Cc1cccc(-c2nc3n(c2-c2cc4cnccc4s2)CC(C(N)=O)N3)n1]

H$_2$SO$_4$ (0.5 mL) was added to a mixture of 1-acetyl-6-(6-methyl-pyridin-2-yl)-5-thieno[3,2-c]pyridin-2-yl-2,3-dihydro-1H-imidazo[1,2-a]imidazole-2-carbonitrile (Example 36, 50 mg, 0.13 mmol) in MeOH (0.5 mL), and the mixture was stirred for 30 minutes. The reaction mixture was neutralized with sat. aqueous NaHCO$_3$ solution and 1N NaOH. The mixture was extracted three times with MeOH/CH$_2$Cl$_2$. The organic layers were combined, dried over Na$_2$SO$_4$, filtered, and concentrated under a reduced pressure. The residue was purified by recrystallization from the mixture of CH$_2$Cl$_2$/MeOH/Hexane to afford the title compound (28.4 mg, 60%) as an off-white solid.

MS (ESI) m/z 359.27 (M-H$_2$O)

$^1$H NMR (300 MHz, CDCl$_3$) δ 8.85 (d, 1H), 8.24 (d, 1H), 7.66 (d, 1H), 7.56 (s, 1H), 7.51 (d, 1H), 7.36 (d, 1H), 7.02 (d, 1H), 5.10 (dd, 1H), 4.49 (m, 2H), 2.47 (s, 3H).

Example 39: Preparation of (6-(6-methylpyridin-2-yl)-5-(thieno[3,2-c]pyridin-2-yl)-2,3-dihydro-1H-imidazo[1,2-a]imidazol-2-yl)methanamine

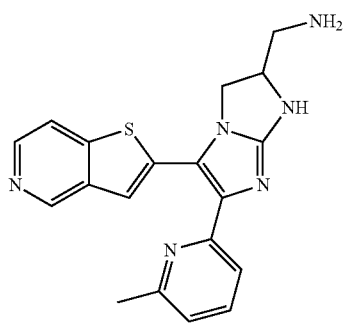 [SMILES: Cc1cccc(-c2nc3n(c2-c2cc4cnccc4s2)CC(CN)N3)n1]

LiAlH$_4$ solution (1.0 M in tetrahydrofuran, 1.5 mL) was added to a solution of 1-acetyl-6-(6-methyl-pyridin-2-yl)-5-thieno[3,2-c]pyridin-2-yl-2,3-dihydro-1H-imidazo[1,2-a]imidazole-2-carbonitrile (Example 36, 200 mg, 0.5 mmol) in dry tetrahydrofuran (5 mL) at 0° C. under N$_2$, and the mixture was stirred for 3 hours. After cooling down to −10° C., the solution was quenched with H$_2$O (57 μL), 1N NaOH (114 μL), and H$_2$O (171 μL) sequentially. The resulting slurry was filtered. The mixture was diluted with H$_2$O and EtOAC, and stirred for 5 minutes. After separating organic layer, the aqueous layer was extracted three times with CH$_2$Cl$_2$. The organic layer was dried over Na$_2$SO$_4$, filtered, and concentrated under a reduced pressure. The residue was purified by MPLC on NH silica gel eluting with MeOH/CH$_2$Cl$_2$ (5%) to afford the title compound (115 mg, 63%) as a bright yellow solid.

MS (ESI) m/z 363.28 (MH+)

$^1$H NMR (300 MHz, CDCl$_3$) δ 9.00 (d, 1H), 8.39 (m, 1H), 7.70 (m, 2H), 7.56 (m, 2H), 7.03 (m, 1H), 4.40 (m, 2H), 4.09 (m, 1H), 3.04 (dd, 1H), 2.92 (dd, 1H), 2.59 (s, 3H).

Example 40: Preparation of N-((6-(6-methylpyridin-2-yl)-5-(thieno[3,2-c]pyridin-2-yl)-2,3-dihydro-1H-imidazo[1,2-a]imidazol-2-yl)methyl)acetamide

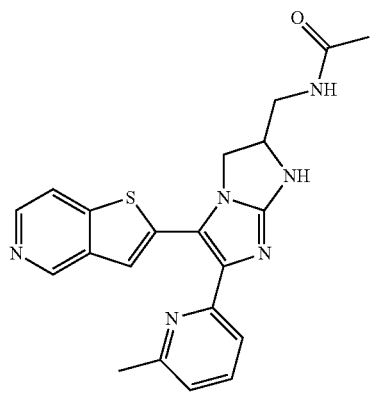 [SMILES: CC(=O)NCC1Cn2c(nc(-c3cccc(C)n3)c2-c2cc3cnccc3s2)N1]

Acetic anhydride (20.8 μL, 0.22 mmol) was added to a solution of (6-(6-methylpyridin-2-yl)-5-(thieno[3,2-c]pyridin-2-yl)-2,3-dihydro-1H-imidazo[1,2-a]imidazol-2-yl)methanamine (Example 39, 36 mg, 0.1 mmol) and N,N-diisopropylethylamine (19.1 μL, 0.11 mmol) in dry CH$_2$Cl$_2$ (1 mL) under N$_2$, and the mixture was stirred for 1 hour. The mixture was diluted with H$_2$O and CH$_2$Cl$_2$, and stirred for 5 minutes. After separating organic layer, the aqueous layer was extracted two times with CH$_2$Cl$_2$. The organic layer was dried over Na$_2$SO$_4$, filtered, and concentrated under a reduced pressure. The residue was purified by MPLC on NH silica gel eluting with MeOH/CH$_2$Cl$_2$ (5%) to obtain the title compound (12 mg, 30%) as a yellow solid.

MS (ESI) m/z 405.24 (MH+)

$^1$H NMR (300 MHz, CDCl$_3$) δ 8.95 (s, 1H), 8.34 (d, 1H), 7.72 (d, 1H), 7.60 (m, 2H), 7.44 (d, 1H), 7.08 (d, 1H), 4.54 (m, 1H), 4.37 (dd, 1H), 4.00 (dd, 1H), 3.52 (m, 2H), 2.58 (s, 3H), 1.99 (s, 3H).

Example 41: Preparation of 6-(6-methylpyridin-2-yl)-5-(thieno[3,2-c]pyridin-2-yl-2,3-dihydroimidazo[2,1-b]oxazole

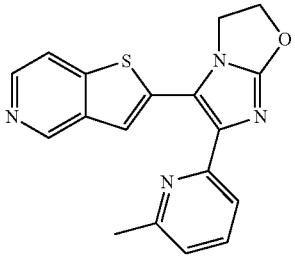 [SMILES: Cc1cccc(-c2nc3n(c2-c2cc4cnccc4s2)CCO3)n1]

The procedure described for Example 6 was repeated except that 5-bromo-6-(6-methylpyridin-2-yl)-2,3-dihydroimidazo[2,1-b]oxazole (Intermediate 14, 35 mg, 0.125 mmol) was used instead of 1-[5-bromo-6-(6-methyl-pyridin-2-yl)-2,3-dihydro-imidazo[1,2-a]imidazol-1-yl]-ethanone and MPLC on NH silica gel elution was conducted with CH$_2$Cl$_2$/hexane/EtOAC (3/1/0.5→3/0/1→3/0/2), to obtain the title compound (8 mg, 19%) as a tan solid.

MS (ESI) m/z 335.17 (MH+)

$^1$H NMR (300 MHz, CDCl$_3$) δ 9.03 (d, 1H), 8.42 (d, 1H), 7.86 (d, 1H), 7.72 (dt, 1H), 7.63 (m, 2H), 7.05 (ddd, 1H), 5.13 (dd, 2H), 4.44 (dd, 2H), 2.58 (s, 3H).

BIOLOGICAL DATA

The biological activity of the compound of the present invention was assessed using the following assays:

Test Example 1: Cell-Free Assay for Evaluating Inhibition of ALK5 Kinase Phosphorylation The kinase activity of ALK5 was assessed by measuring radiolabelled phosphate[$^{33}$P] incorporation into the generic substrate, casein. The kinase domain of human ALK5 (200$^{th}$ to 503$^{rd}$ amino acids) was fused to the N-terminal GST/histidine tag and the kinase construct was engineered to be expressed from insect cells. The purified ALK5 protein was mixed with the casein substrate (final concentration, 2 mg/mL), and reaction buffer (containing 20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT and 1% DMSO) was added thereto. DMSO solution of each test compound of formula (I) having different concentrations was prepared using pure DMSO, and each solution was delivered to the reaction mixture. $^{33}$P-ATP (specific activity 0.01 μCi/μl final) was delivered into the reaction mixture thus obtained for initiating the reaction, followed by incubation at room temperature for 2 hours. After incubation, the reaction solution was spotted onto P81 ion exchange paper, the paper was washed extensively with 0.75% phosphoric acid. Then, the paper was air-dried and counted.

The inventive compounds typically exhibited IC$_{50}$ values of less than 10 μM; some exhibited IC$_{50}$ values of less than 1 μM; and some even exhibited IC$_{50}$ values less than 50 nM (see Table 1).

TABLE 1

| Example | IC$_{50}$ (nM) |
|---------|----------------|
| 2 | 6.6 |
| 3 | 31.6 |
| 4 | 12.1 |
| 6 | 6.1 |
| 7 | 10.3 |
| 9 | 11.5 |
| 15 | 38.1 |

Test Example 2: Cell-Free Assay for Evaluating Inhibition of ALK4 Kinase Phosphorylation The kinase activity of ALK4 was assessed by measuring radiolabelled phosphate[$^{33}$P] incorporation into the generic substrate, casein. The kinase domain of human ALK4 (150$^{th}$ to 505$^{th}$ amino acids) was fused to GST tag and the kinase construct was engineered to be expressed from insect cells.

Inhibition of the ALK4 kinase phosphorylation by test compounds of formula (I) was determined in a manner similar to that described in Test Example 1 except for using ALK4 instead of ALK5.

The inventive compounds typically exhibited IC$_{50}$ values of less than 10 µM; some exhibited IC$_{50}$ values of less than 1 µM; and some even exhibited IC$_{50}$ values of less than 50 nM.

Test Example 3: Assay for Evaluating Cellular Inhibition of TGF-β Signaling

Biological activity of the inventive compound of formula (I) was determined by measuring their ability to inhibit TGFβ1-induced-Smad binding element-luciferase (SBE-Lux) reporter activity and PAI-1-luciferase (p3TP-Lux) reporter activity in HaCaT cells. HaCaT cells were cultured in DMEM medium (containing 10% FBS, 100 U/mL penicillin, and 100 µg/mL streptomycin) at 37° C. in a 5% CO$_2$ incubator. The cells were plated at a concentration of 2.5× 10$^4$ cells/well in 96 well plates, and transfected with 0.6 µg of p3TP-Lux and SBE-Lux reporter construct, respectively. 24 hours after the trasnfection, the cells were pre-treated with varying concentration (5, 10, 50, 100 and 500 nM) of ALK5 inhibitor for 2 hours. The cells thus obtained were then stimulated with 5 ng/ml of TGF-β1 ligand (PEPRO-TECH, 100-21C) and incubated at 37° C. in a 5% CO$_2$ incubator for 24 hours. The media was washed out, and the luciferase activity in cell lysates was determined by luciferase assay system (Promega).

The IC$_{50}$ value of the inventive compound of formula (I) was calculated from dose-response curves generated using Prism software.

The inventive compound of formula (I) typically exhibited IC$_{50}$ values of less than 10 µM; some exhibited IC$_{50}$ values of less than 1 µM; and some even exhibited IC$_{50}$ values of less than 50 nM.

While the invention has been described with respect to the above specific embodiments, it should be recognized that various modifications and changes may be made to the invention by those skilled in the art which also fall within the scope of the invention as defined by the appended claims.

What is claimed is:

1. A compound of formula (I), a pharmaceutically acceptable salt or solvate thereof:

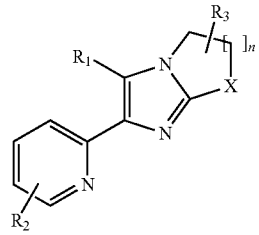

(I)

wherein,

R$_1$ is

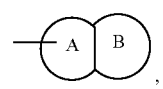

wherein A is phenyl, pyridyl or thienyl and B is a 5-7 membered aromatic ring, wherein said ring B optionally contains up to three heteroatoms independently selected from O, N and S, and R$_1$ is optionally substituted with one or more groups independently selected from the group consisting of halogen, —O—C$_{1-6}$ alkyl, —S—C$_{1-6}$ alkyl, —C$_{1-6}$ alkyl, —C$_{1-6}$ haloalkyl, CN, —(CH$_2$)$_p$—OR$_4$, —O—(CH$_2$)$_q$—NR$_4$R$_5$, —(CH$_2$)$_p$—NR$_4$R$_5$, —NHCO—O—(CH$_2$)$_q$—NR$_4$R$_5$, —NHCO—(CH$_2$)$_p$—NR$_4$R$_5$, and —C$_{5-15}$ heteroaryl containing up to three heteroatoms independently selected from the group consisting of O, N and S; or R$_1$ is pyridyl optionally substituted with one or more groups independently selected from the group consisting of halogen, —O—C$_{1-6}$ alkyl, —S—C$_{1-6}$ alkyl, —C$_{1-6}$ alkyl, —C$_{1-6}$ haloalkyl, —CN, —(CH$_2$)$_p$—OR$_4$, —O—(CH$_2$)$_q$—NR$_4$R$_5$, —NH—(CH$_2$)$_q$—NR$_4$R$_5$, —(CH$_2$)$_p$—NR$_4$R$_5$, —(CH$_2$)$_p$—NHCOR$_4$, —(CH$_2$)$_p$—NHCO$_2$R$_4$, —(CH$_2$)$_p$—NHSO$_2$R$_4$ or —C$_{5-15}$ heterocycle, said —C$_{5-15}$ heterocycle containing up to three heteroatoms independently selected from the group consisting of O, N and S and being optionally substituted with C$_{1-6}$ alkyl;

R$_2$ is —O—C$_{1-6}$ alkyl, —S—C$_{1-6}$ alkyl, —C$_{1-6}$ alkyl, —C$_{3-7}$ cycloalkyl, —C$_{5-15}$ heteroaryl, —C$_{1-6}$ haloalkyl, —(CH$_2$)$_p$—OR$_4$, —O—(CH$_2$)$_p$—NR$_4$R$_5$, —(CH$_2$)$_p$—NR$_4$R$_5$, CN, —CONHR$_4$, or —SO$_2$NHR$_4$;

R$_3$ is H, —O—C$_{1-6}$ alkyl, —S—C$_{1-6}$ alkyl, —C$_{3-7}$ cycloalkyl, —O—(CH$_2$)$_q$—NR$_4$R$_5$, —(CH$_2$)$_p$—CON-HOH, —CN—, —CH$_2$—CN, —(CH$_2$)$_2$—CN—, —CO$_2$R$_4$, —CH$_2$—CO$_2$R$_4$—, —CONR$_4$R$_5$, —CH$_2$—CONR$_4$R$_5$, —(CH$_2$)$_p$—CH═CH—CN, —(CH$_2$)$_p$—CH═CH—CO$_2$R$_4$, —(CH$_2$)$_p$—CH═CH—CONR$_4$R$_5$, —NHCO$_2$R$_4$, —CH$_2$—NHCO$_2$R$_4$ or —(CH$_2$)$_p$—CH═CH-tetrazole;

R$_4$ and R$_5$ are independently H or —C$_{1-6}$ alkyl; or R$_4$ and R$_5$, together with the nitrogen atom to which they are attached, form a 3 to 6-membered aromatic or non-aromatic ring, wherein said ring optionally contains up to three heteroatoms independently selected from the group consisting of O, N, and S;

R$_6$ is —C$_{1-6}$ alkyl;

p is an integer ranging from 1 to 4;

q is an integer ranging from 2 to 5;

n is an integer ranging from 1 to 3;

X is NR$_7$; and

R$_7$ is H, OH, —C$_{1-6}$ alkyl, —C$_{3-7}$ cycloalkyl, or —CO—C$_{1-6}$ alkyl.

2. The compound of claim 1, a pharmaceutically acceptable salt or solvate thereof, wherein
R$_1$ is

, wherein A is phenyl, pyridyl or thienyl and B is a 5-6 membered aromatic ring, wherein said ring B optionally contains one or two heteroatoms independently selected from O, N and S, and R$_1$ is optionally substituted with one or more groups independently selected from the group consisting of halogen, —O—C$_{1-6}$ alkyl, —S—C$_{1-6}$ alkyl, —C$_{1-6}$ alkyl, —C$_{1-6}$ haloalkyl, —CN, —(CH$_2$)$_p$—OR$_4$, —O—(CH$_2$)$_q$—NR$_4$R$_5$, —(CH$_2$)$_p$—NR$_4$R$_5$, —NHCO—O—(CH$_2$)$_q$—NR$_4$R$_5$, —NHCO—(CH$_2$)$_p$—NR$_4$R$_5$, and —C$_{5-15}$ heteroaryl containing up to three heteroatoms independently selected from the group consisting of O, N and S;

R$_2$ is halogen, —O—C$_{1-6}$ alkyl, —S—C$_{1-6}$ alkyl, —C$_{1-6}$ alkyl, —C$_{3-7}$ cycloalkyl, —C$_{5-15}$ heteroaryl, —C$_{1-6}$ haloalkyl, —(CH$_2$)$_p$—OR$_4$, —O—(CH$_2$)$_p$—NR$_4$R$_5$, —(CH$_2$)$_p$—NR$_4$R$_5$, —CN, —CONHR$_4$, or —SO$_2$NHR$_4$;

R$_3$ is H, —O—C$_{1-6}$ alkyl, —S—C$_{1-6}$ alkyl, —C$_{1-6}$ alkyl, C$_{3-7}$ cycloalkyl, —(CH$_2$)$_p$—NR$_4$R$_5$, —O—(CH$_2$)$_q$—NR$_4$R$_5$, —(CH$_2$)$_p$—CONHOH, —CN, —CH$_2$—CN, —(CH$_2$)$_2$—CN, —CO$_2$R$_4$, —CH$_2$—CO$_2$R$_4$, —CONR$_4$R$_5$, —CH$_2$—CONR$_4$R$_5$, —CH$_2$—CH=CH-tetrazole, —NHCO$_2$R$_4$, or —CH$_2$—NHCO$_2$R$_4$;

R$_4$ and R$_5$ are independently H or —C$_{1-4}$ alkyl; or R$_4$ and R$_5$ together with the nitrogen atom to which they are attached, form a 3 to 6-membered aromatic or non-aromatic heterocyclic ring containing up to three heteroatoms independently selected from the group consisting of O, N and S;

p is an integer ranging from 1 or 2;
q is an integer ranging from 2 to 4;
n is an integer of 1 or 2;
X is NR$_7$; and
R$_7$ is H, OH, —C$_{1-6}$ alkyl, or —CO—C$_{1-6}$ alkyl.

3. The compound of claim 1, a pharmaceutically acceptable salt or solvate thereof, wherein
R$_1$ is a fused ring selected from the group consisting of quinoxalinyl, quinolinyl, thienopyridinyl, benzothiazolyl, benzothiophenyl, triazolopyridinyl, benzoxazolyl, and quinolinyl, wherein said fused ring is optionally substituted with one or more groups independently selected from the group consisting of halogen, —O—C$_{1-6}$ alkyl, —S—C$_{1-6}$ alkyl, —C$_{1-6}$ alkyl, —C$_{1-6}$ haloalkyl, CN, —(CH$_2$)$_p$—OR$_4$, —O—(CH$_2$)$_q$—NR$_4$R$_5$, —(CH$_2$)$_p$—NR$_4$R$_5$, or —C$_{5-15}$ heteroaryl, said heteroaryl containing one or two heteroatoms independently selected from O, N and S;

R$_2$ is —C$_{1-6}$ alkyl, —C$_{1-6}$ haloalkyl, or —NH$_2$, and is positioned ortho to the nitrogen of the pyridyl ring;
R$_3$ is H, —O—C$_{1-6}$ alkyl, —S—C$_{1-6}$ alkyl, —CN, —CH$_2$—CN, (CH$_2$)$_2$—CN, —CO$_2$R$_4$, —CH$_2$—CO$_2$R$_4$, —CONR$_4$R$_5$, or —CH$_2$—CONR$_4$R$_5$;
R$_4$ and R$_5$ are independently H or —C$_{1-6}$ alkyl;
p is an integer ranging from 1 or 2;
q is an integer ranging from 2 to 4;
n is an integer ranging from 1 to 3;
X is NR$_7$; and
R$_7$ is H, or —CO—C$_{1-6}$alkyl.

4. A compound which is selected from the group consisting of:
1) 1-[6-6-Methyl-pyridin-2-yl)-5-quinoxalin-6-yl-2,3-dihydro-imidazo[1,2-a]imidazol-1-yl]-ethanone;
2) 6-[2-(6-Methyl-pyridin-2-yl)-6,7-dihydro-5H-imidazo[1,2-a]imidazol-3-yl]-quinoxaline;
3) 6-[2-(6-Methyl-pyridin-2-yl)-5,6,7,8-tetrahydro-imidazo[1,2-a]pyrimidin-3-yl]-quinoxaline;
4) 6-[2-(6-Methyl-pyridin-2-yl)-6,7-dihydro-5H-imidazo[1,2-a]imidazol-3-yl]-quinoline;
5) 6-[2-(6-Methyl-pyridin-2-yl)-5,6,7,8-tetrahydro-imidazo[1,2-a]pyrimidin-3-yl]-quinoline;
6) 2-[2-(6-Methyl-pyridin-2-yl)-6,7-dihydro-5H-imidazo[1,2-a]imidazol-3-yl]-thieno[3,2-c]pyridine;
7) 6-[2-(6-Methyl-pyridin-2-yl)-6,7-dihydro-5H-imidazo[1,2-a]imidazol-3-yl]-benzothiazole;
8) 5-Benzo[b]thiophen-5-yl-6-(6-methyl-pyridin-2-yl)-2,3-dihydro-1H-imidazo[1,2-a]imidazole;
9) 6-[2-(6-Methyl-pyridin-2-yl)-6,7-dihydro-5H-imidazo[1,2-a]imidazol-3-yl]-[1,2,4]triazolo[1,5-a]pyridine;
10) 5-[2-(6-Methyl-pyridin-2-yl)-6,7-dihydro-5H-imidazo[1,2-a]imidazol-3-yl]-benzoxazole;
11) 4-[2-(6-Methyl-pyridin-2-yl)-6,7-dihydro-5H-imidazo[1,2-a]imidazol-3-yl]-quinoline;
12) 7-[2-(6-Methyl-pyridin-2-yl)-6,7-dihydro-5H-imidazo[1,2-a]imidazol-3-yl]-2-pyrazol-1-yl-quinoxaline;
13) Dimethyl-(2-{7-[2-(6-methyl-pyridin-2-yl)-6,7-dihydro-5H-imidazo[1,2-a]imidazol-3-yl]-quinoxalin-2-yloxy}-ethyl)-amine;
14) 2-Methoxy-7-[2-(6-methyl-pyridin-2-yl)-6,7-dihydro-5H-imidazo[1,2-a]imidazol-3-yl]-quinoxaline;
15) 2-Methyl-6-(6-(6-methylpyridin-2-yl)-2,3-dihydro-1H-imidazo[1,2-a]imidazol-5-yl)quinoline;
16) 1-Acetyl-6-(6-methyl-pyridin-2-yl)-5-thieno[3,2-c]pyridin-2-yl-2,3-dihydro-1H-imidazo[1,2-a]imidazole-2-carboxylic acid ethyl ester;
17) 6-(6-Methyl-pyridin-2-yl)-5-thieno[3,2-c]pyridin-2-yl-2,3-dihydro-1H-imidazo[1,2-a]imidazole-2-carboxylic acid ethyl ester;
19) 1-Acetyl-6-(6-methyl-pyridin-2-yl)-5-thieno[3,2-c]pyridin-2-yl-2,3-dihydro-1H-imidazo[1,2-a]imidazole-2-carbonitrile;
20) 6-(6-Methyl-pyridin-2-yl)-5-thieno[3,2-c]pyridin-2-yl-2,3-dihydro-1H-imidazo[1,2-a]imidazole-2-carbonitrile; and
21) 6-(6-Methyl-pyridin-2-yl)-5-thieno[3,2-c]pyridin-2-yl-2,3-dihydro-1H-imidazo[1,2-a]imidazole-2-carboxylic acid amide,
or a pharmaceutically acceptable salt or solvate thereof.

5. A method for manufacturing a medicament, comprising combining the compound of formula (I) or a pharmaceutically acceptable salt or solvate of claim 1 as an active ingredient with a pharmaceutically acceptable carrier or diluent to make the medicament.

6. A pharmaceutical composition comprising the compound of formula (I) or its pharmaceutically acceptable salt or solvate of claim 1 as an active ingredient, and a pharmaceutically acceptable diluent or carrier.

7. A method for inhibiting ALK5 kinase phosphorylation or ALK4 kinase phosphorylation in a mammal, which comprises administering the compound of formula (I) or its pharmaceutically acceptable salt or solvate of claim 1 to the mammal in need thereof.

8. A method for inhibiting ALK5 and/or ALK4 receptors in a mammal, which comprises administering the compound of formula (I) or its pharmaceutically acceptable salt or solvate of claim 1 to the mammal in need thereof.

\* \* \* \* \*